(12) United States Patent
Capek et al.

(10) Patent No.: US 11,331,476 B2
(45) Date of Patent: May 17, 2022

(54) PROSTHETIC HEART VALVE AND METHODS FOR CARDIAC HEMODYNAMIC OPTIMIZATION AND MONITORING

(71) Applicant: Tendyne Holdings, Inc., St. Paul, MN (US)

(72) Inventors: John M. Capek, Winnetka, IL (US); Michael J. Urick, Chaska, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 0 days.

(21) Appl. No.: 16/761,546

(22) PCT Filed: Nov. 20, 2018

(86) PCT No.: PCT/US2018/061936
§ 371 (c)(1),
(2) Date: May 5, 2020

(87) PCT Pub. No.: WO2019/108440
PCT Pub. Date: Jun. 6, 2019

(65) Prior Publication Data
US 2020/0282204 A1 Sep. 10, 2020

Related U.S. Application Data

(60) Provisional application No. 62/592,716, filed on Nov. 30, 2017.

(51) Int. Cl.
*A61F 2/24* (2006.01)
*A61N 1/05* (2006.01)
(Continued)

(52) U.S. Cl.
CPC ........... *A61N 1/059* (2013.01); *A61N 1/3629* (2017.08); *A61N 1/37* (2013.01); *A61F 2250/0004* (2013.01)

(58) Field of Classification Search
CPC .... A61N 1/36002; A61N 1/0408; A61N 1/05; A61N 1/36034; A61N 1/36017; A61N 1/3787; A61F 2/24–2496
See application file for complete search history.

(56) References Cited

U.S. PATENT DOCUMENTS

| 5,385,574 A | 1/1995 | Hauser et al. |
| 10,543,083 B2 * | 1/2020 | Gross .................... A61F 2/2418 |

(Continued)

FOREIGN PATENT DOCUMENTS

| WO | 2015120122 A2 | 8/2015 |
| WO | 2017096157 A1 | 6/2017 |

OTHER PUBLICATIONS

International Search Report including Written Opinion from Application No. PCT/US18/61936 dated Jan. 25, 2019, 18 pages.

*Primary Examiner* — Michael W Kahelin
*Assistant Examiner* — Michael A Rizzuto
(74) *Attorney, Agent, or Firm* — Lerner, David, Littenberg, Krumholz & Mentlik, LLP

(57) ABSTRACT

In some embodiments, a method includes delivering to a native valve annulus (e.g., a native mitral valve annulus) of a heart a prosthetic heart valve (200) having a body (242) expandable from a collapsed, delivery configuration to an expanded, deployed configuration. The method can further include, after the delivering, causing the prosthetic heart valve to move from the delivery configuration to the deployed configuration. With the prosthetic heart valve in its deployed configuration, an anchoring tether (191) extending from the prosthetic heart valve can be secured to a wall (Vw) of the heart (H). An electrode (189) coupled to at least one of the prosthetic heart valve or the anchoring tether can then be used to at least one of pace the heart or sense a signal associated with the heart.

9 Claims, 19 Drawing Sheets

(51) Int. Cl.
*A61N 1/362* (2006.01)
*A61N 1/37* (2006.01)

(56) References Cited

U.S. PATENT DOCUMENTS

| | | | |
|---|---|---|---|
| 2003/0023295 A1* | 1/2003 | Osypka | A61N 1/056 607/122 |
| 2006/0259137 A1 | 11/2006 | Artof et al. | |
| 2009/0234407 A1* | 9/2009 | Hastings | A61N 1/36842 607/14 |
| 2011/0144743 A1* | 6/2011 | Lattouf | A61B 17/0401 623/2.11 |
| 2012/0197388 A1* | 8/2012 | Khairkhahan | A61B 17/068 623/2.11 |
| 2014/0057940 A1 | 2/2014 | Mankowski et al. | |
| 2015/0119978 A1* | 4/2015 | Tegels | A61F 2/2418 623/2.11 |
| 2015/0223934 A1* | 8/2015 | Vidlund | A61F 2/2412 623/2.11 |
| 2016/0143736 A1 | 5/2016 | Vidlund et al. | |
| 2016/0367368 A1 | 12/2016 | Vidlund et al. | |
| 2017/0079790 A1 | 3/2017 | Vidlund et al. | |
| 2017/0128208 A1 | 5/2017 | Christianson et al. | |
| 2017/0143320 A1 | 5/2017 | Jimenez et al. | |
| 2017/0258585 A1* | 9/2017 | Marquez | A61F 2/2412 |
| 2017/0258586 A1 | 9/2017 | Bateman et al. | |
| 2017/0319333 A1 | 11/2017 | Tegels et al. | |

\* cited by examiner

PROSTHETIC HEART VALVE AND METHODS FOR CARDIAC HEMODYNAMIC OPTIMIZATION AND MONITORING

CROSS-REFERENCE TO RELATED APPLICATIONS

The present application is a national phase entry under 35 U.S.C. § 371 of International Application No. PCT/US2018/061936 filed Nov. 20, 2018, published in English, which claims the benefit of U.S. Provisional Patent Application No. 62/592,716, filed Nov. 30, 2017, entitled PROSTHETIC HEART VALVE AND METHODS FOR CARDIAC HEMODYNAMIC OPTIMIZATION AND MONITORING, the disclosures of which are incorporated herein by reference in their entireties.

BACKGROUND OF THE DISCLOSURE

Embodiments described herein relate generally to prosthetic heart valves, and devices and methods for cardiac hemodynamic optimization and monitoring. More particularly, embodiments described herein relate to devices and methods for cardiac hemodynamic optimization and monitoring of patients having an implanted prosthetic heart valve.

The human heart is responsible for pumping blood around the human body. The human heart is separated into four distinct chambers, and is commonly referenced in terms of the right or left side of the heart. The right side of the heart, including the right atrium and the right ventricle, is responsible for receiving de-oxygenated blood from the body, and then pumping the de-oxygenated blood to the lungs in order to oxygenate the blood. The left side of the heart, including the left atrium and left ventricle, is responsible for receiving oxygenated blood from the lungs, and then pumping the oxygenated blood to various parts of the body. More specifically, the left side of the heart includes a left ventricular outflow tract (LVOT) along which oxygenated blood flows during systole (as described in more detail below) from the left ventricle to the aorta, which anatomically sits immediately behind the anterior segment of the mitral annulus. The movement of blood within the chambers of the heart is controlled by four valves: aortic, mitral, pulmonic and tricuspid. These valves open and close constantly, and as such, can be subject to wear and tear and other challenges that affect their performance (e.g., mitral valve regurgitation, prolapse, and/or stenosis), and consequently, the entire circulatory system.

Some known devices for repairing the performance of the heart, such as, for example, the performance of a mitral valve of the heart, can include a prosthetic heart valve. The prosthetic heart valve can be implanted and secured to a native annulus of the heart. Prosthetic heart mitral valve implantation, however, can be associated with displacement of the native mitral valve apparatus and/or interference or obstruction with the LVOT (i.e., interference with blood flow out of the left ventricle of the heart). For example, some known prosthetic mitral valves include subvalvular components that obstruct the LVOT and/or direct blood flow from the atrium to the ventricle in a manner that creates LVOT interruption and/or undesirable flow gradients, turbulence, eddies, and/or otherwise undesirable flow profiles within the heart. As another example, some patients' anatomy is not conducive to prosthetic valve implantation while sufficiently preserving the LVOT, and in some instances, can exacerbate LVOT interruption issues. For instance, some patients have a small LVOT and/or a septal bump (also referred to as a "septal bulge") within the left ventricle that interferes with and/or inhibits blood flow through the LVOT. In some instances, a septal bump alone or in combination with an implanted prosthetic mitral valve can reduce the LVOT such that an undesirable fluid flow profile (e.g., a fluid jet) can occur from the left ventricle to the aorta. Such a septal bump, for example, is an anatomical feature particularly common to patients needing heart valve replacement or repair. In fact, although patient screening prior to prosthetic mitral valve implantation can help predict potential risk of LVOT interruption, such screening often prevents patients with considerable risk of LVOT issues (e.g., due to a septal bump and/or abnormally small LVOT), who otherwise would benefit from mitral valve replacement, from undergoing mitral valve replacement with a prosthetic mitral valve apparatus. Some known procedures attempt to address such LVOT issues by altering the geometry and/or function of the heart by using tissue ablation. Ablation, however, may include an invasive procedure, introduce additional risks to the patient, and/or undesirably permanently alter the heart.

Thus, a need exists for devices and methods for safely and effectively delivering and deploying a prosthetic heart valve within a heart of a patient while limiting risks of LVOT interruption, including patients who have a considerable risk of LVOT interruption due to, for example, a small LVOT and/or a septal bump.

Further, LVOT interruption (e.g., with a prosthetic mitral valve implanted within the heart) often includes an undesirable flow gradient within the LVOT and often requires one or more additional procedures to remove the prosthetic mitral valve or correct or recover the LVOT, or in some cases requires additional medication. Even further, notwithstanding LVOT interruption, some patients with prosthetic mitral valve implants experience other problems associated with mitral valve replacement. Accordingly, a need exists for devices and methods for monitoring various regions (e.g., the left ventricle, the left atrium, etc.) of the heart and heart function generally after prosthetic heart valve implantation.

BRIEF SUMMARY

Apparatus, systems and methods for managing a native heart valve apparatus, and particularly a native anterior leaflet of a native heart valve, when a prosthetic heart valve is delivered to, or disposed in, a native annulus of the heart are described herein. In some embodiments, a method for managing a native heart valve apparatus includes delivering to a native valve annulus (e.g., a native mitral valve annulus) of a heart a prosthetic heart valve having a body expandable from a collapsed, delivery configuration to an expanded, deployed configuration. The method can further include, after the delivering, causing the prosthetic heart valve to move from the delivery configuration to the deployed configuration. With the prosthetic heart valve in its deployed configuration, an anchoring tether extending from the prosthetic heart valve can be secured to a wall of the heart. An electrode coupled to at least one of the prosthetic heart valve or the anchoring tether can then be used to at least one of pace the heart or sense a signal associated with the heart.

DETAILED DESCRIPTION

Figure 1:
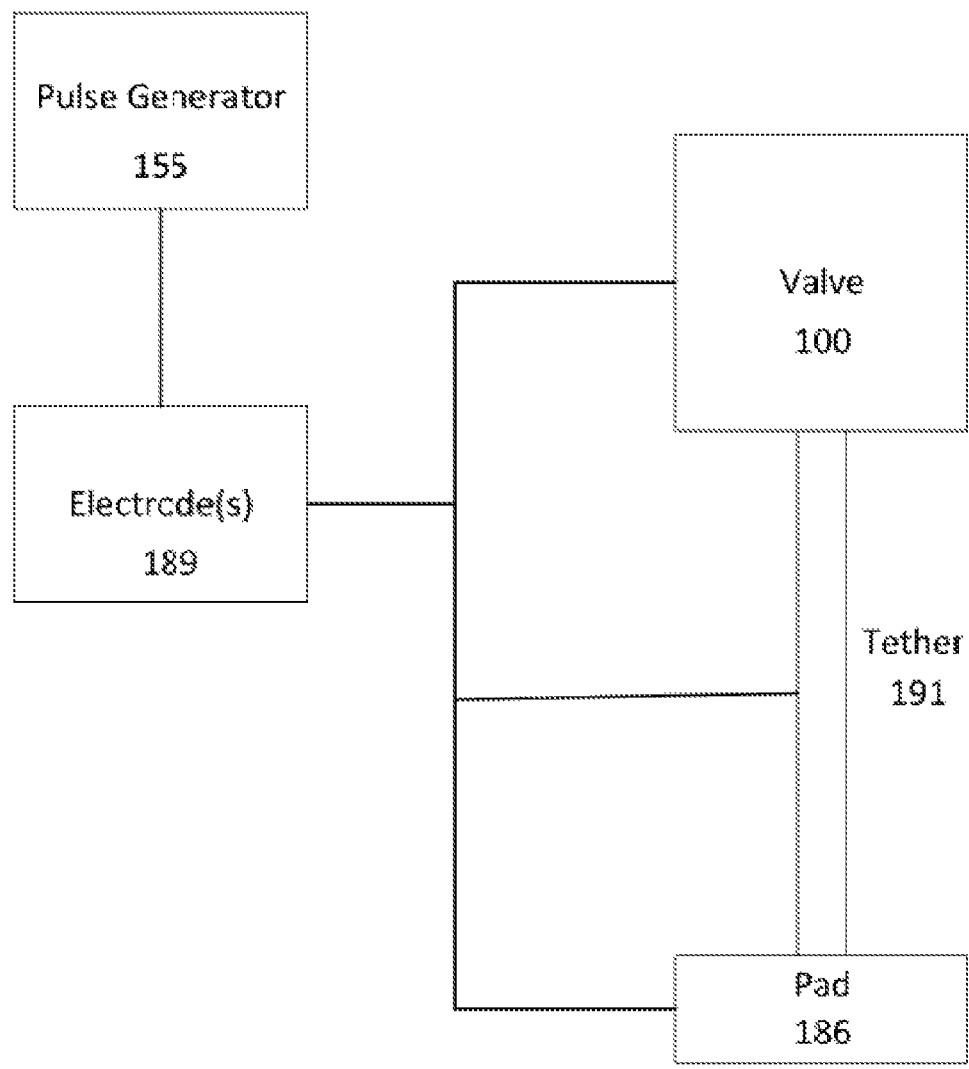
FIG. 1 is a schematic illustration of a cardiac hemodynamic optimization and monitoring system, according to an embodiment.

Apparatus, systems, and methods are described herein for inhibiting, limiting and/or preventing LVOT interruption and/or obstruction in conjunction with an implanted prosthetic valve (e.g., an implanted prosthetic mitral valve) having a tether extending from the implanted prosthetic valve through the left ventricle and out an incision in the apical region of the heart. The tether can aid in holding the implanted prosthetic valve in place in the native valve annulus (the prosthetic valve and the tether are referred to herein collectively as a "valve-tether"). In some embodiments, with the valve-tether implanted within the native annulus of the heart, an artificial electrical pulse generator (e.g, pacemaker) may be used to supplement the heart's natural conduction system (as described in more detail below) to manipulate the geometry and/or function of the heart such that LVOT interruption or obstruction is limited, prevented, or otherwise inhibited. In such embodiments, the valve-tether can be used to selectively deliver electrical signals or pulses to one or more regions of the heart to selectively optimize or otherwise affect the geometry and/or function of the heart, for example, to promote a sufficient LVOT.

A heartbeat is a complex series of events controlled by the heart's natural conduction system. These events take place inside and around the heart. A heartbeat is a single cycle in which the heart's chambers relax and contract to pump blood. This cycle includes the opening and closing of the inlet and outlet valves of the right and left ventricles of the heart. Each heartbeat includes two parts: diastole and systole. During diastole, the atria and ventricles of the heart relax and begin to fill with blood. At the end of diastole, the heart's atria contract (atrial systole) and pump blood into the ventricles. The atria then begin to relax. The ventricles then contract (ventricular systole), pumping blood out of the heart. Each beat of the heart is set in motion by an electrical signal from within the heart muscle. In a normal, healthy heart, each beat begins with a signal from the sinoatrial (SA) node (also referred to as the heart's "natural pacemaker"), located in the right atrium of the heart. A pulse, or heart rate, is the number of signals the SA node produces per minute. The signal spreads across the cells of the heart's right and left atria, causing the atria to contract. This action pushes blood through the open valves from the atria into both ventricles. The signal arrives at the atrioventricular (AV) node near the ventricles, slows for an instant to allow the heart's right and left ventricles to fill with blood, and is then released and spreads across the cells of the ventricle walls, causing both ventricles to contract. As the right ventricle contracts, blood is pushed through the pulmonary valve to the lungs, and as the left ventricle contracts, blood is pushed through the aortic valve to other portions of the body. As the signal passes, the walls of the ventricles relax and await the next signal.

As described above, in some embodiments, the valve-tether can be used to generate and/or deliver electrical pulses to the heart to selectively limit LVOT interruption due to, for example, the prosthetic valve or tether-valve's presence within the heart and/or the particular anatomy of a patient (e.g., presence of a septal bump or an abnormally small LVOT).

In some embodiments, a conductive wire disposed within a tether and electrically coupled to one or more electrodes attached to the tether and/or to a prosthetic valve from which the tether extends, as described herein, can be used to electrically pace (e.g., biventricular pace) the heart to desirably manipulate the LVOT. Pacing the heart in this manner can, for example, allow a medical professional (e.g., surgeon or interventionalist) to selectively manipulate a shape and performance of the ventricle to promote sufficient clearance along the LVOT. For example, with a prosthetic mitral valve implanted within a native mitral valve annulus of a patient having a relatively pronounced septal bump, who is thus susceptible to LVOT interruption, the heart can be selectively paced to alter movement of the septal bump during functioning of the heart, e.g., during systole. In this manner, ventricular contraction can be selectively altered to minimize LVOT obstruction and improve or optimize performance of a heart containing a prosthetic valve, thereby reducing potential complications associated with LVOT obstruction, and providing valve replacement opportunities to patients who otherwise were too high risk due to such LVOT risks and complications. In some embodiments, using the implanted valve-tether to pace the heart for LVOT optimization can be done in combination with other LVOT optimization techniques, such as, for example, the native leaflet management techniques described in U.S. patent application Ser. No. 14/499,129 (the '129 application), U.S. Patent Application Publication No. 2017/0128208 (the '208 application), and/or International Application No. PCT/US16/64610 (the '610 application), all of which are incorporated herein by reference in their entireties.

In addition to or instead of implanting a valve-tether with electrode(s) to pace a heart, the electrode(s) can be used like a defibrillator to, for example, restore an abnormally functioning heart to normal function.

In addition to the apparatus, systems, and methods introduced above and described in detail below, apparatus, systems, and methods are described herein for monitoring cardiac geometry and function in conjunction with an implanted prosthetic valve (e.g., an implanted prosthetic mitral valve). In some embodiments, a prosthetic valve and/or a tether extending from the prosthetic mitral valve can be used to sense various cardiac measurements of interest, such as, for example, left/right ventricular dimensions, left/right ventricular pressure (e.g., diastolic and systolic pressures), left/right ventricular volume, left/right atrium dimensions, left/right atrial pressure and/or volume, blood volume, blood temperature, breathing rate, and/or the like. In this manner, the prosthetic valve and/or tether can provide a minimally invasive way to monitor a patient's response post-implantation. As described in further detail herein, to sense the various cardiac measurements, the tether can be conductive, the tether can be attached to or disposed about a conductive wire, and/or the tether and/or valve can include or have attached thereto one or more electrodes or sensors that, for example, can provide signals to be used in calculations (e.g., impedance calculations) for monitoring the heart. In some embodiments, for example, one or more electrodes can be disposed on an upper or cuff portion of a prosthetic mitral valve such that when the prosthetic mitral valve is implanted within a native mitral valve annulus the electrode can sense and provide atrial diagnostics (e.g., volume and/or pressures within the left atrium of the heart).

FIG. 1 is a schematic illustration of a system for cardiac hemodynamic optimization and monitoring, according to an embodiment. As shown, the system 110 includes a valve 100 coupled to a pad 186 via a tether 191, one or more electrodes 189 physically coupled to at least one of the valve 100, tether 191, or pad 186. The valve 100, for example, can be a prosthetic mitral valve and can be implanted within a native mitral valve annulus of a patient. In alternative instances, the valve 100 can be an aortic or triscuspid valve or the like. The tether 191 and pad 186 can be used to aid in holding the valve 100 in place in the native valve annulus. For example, in some instances, the tether 191 can extend from the valve 100, across the ventricle, and through an incision in the heart. The pad 186 is coupled to the tether 191 and can be used to secure the tether 191 and the valve 100 in a desired position and orientation relative to the heart.

The one or more electrodes 189 can be coupled to any portion or portions of the valve 100, pad 186, and/or tether 191 such that electrical signals can be selectively transmitted from the one or more electrodes 189 to one or more regions of heart tissue to pace the heart. For example, in some embodiments, an electrode 189 can be coupled to the implanted tether 191 near an apical region of the heart such that the electrode 189 is in physical contact with a portion of the heart wall. In this manner, a signal can be delivered to the heart wall to pace the heart and promote a desirable LVOT, as described in further detail herein.

Further as shown in FIG. 1, the one or more electrodes 189 can be operably coupled (e.g., directly and/or physically coupled, or indirectly (e.g., with intervening components) coupled) to a pulse generator 155 configured to generate and deliver to the one or more electrodes 189 electrical signals for selective heart pacing. For example, the tether 191 can be formed of a material that can transfer signals to and from the pulse generator 155. In some embodiments, the tether 191 can define a lumen through which a lead can extend between the one or more electrodes 189 and the pulse generator 155. The pulse generator 155 can be any suitable device configured to perform such functionality. In some instances, for example, the pulse generator 155 can be an implantable pulse generator similar to a pacemaker, or defibrillator. Further, the pulse generator 155 can be disposed in any suitable location within or on the patient's body. For example, the pulse generator 155 can be implanted subdermally or in the subcutaneous abdominal space. In other embodiments, the pulse generator 155 can be disposed external to the patient's body and the electrical energy can be transferred through the patient's skin and other tissues to the electrodes by conductive elements (wires etc.) or non-conductive mechanisms (inductive, capacitive, etc.).

In addition to or instead of the one or more electrodes 189 being configured and used to deliver pacing signals to the heart, as described in further detail herein, one or more electrodes 189 can be configured and used to measure various cardiac conditions within the heart and communicate those conditions to one or more pulse generators 155. For example, in some instances, one or more electrodes can be coupled to the tether 191 when extended across the left ventricle of the heart to measure a condition (e.g., pressure, volume, etc.) of the left ventricle. As described above, each electrode 189 is communicatively coupled to one or more pulse generators 155. In embodiments including electrodes configured and used for both pacing and cardiac measurements, in some instances, a single pulse generator may be used for both providing the pacing signals and for receiving and/or processing the cardiac conditions sensed by the one or more electrodes. In other instances, multiple pulse generators can be used. For example, one pulse generator may be implanted within or on the patient's body for providing pacing signals, while another pulse generator may be implanted within or on the patient's body or disposed completely external to the patient's body, and configured to receive signals from the one or more electrodes 189 representative of cardiac condition(s). For example, in some instances, such signals can be transmitted wirelessly from the one or more electrodes to a pulse generator 155 outside the patient's body (e.g., an electronic device worn by the patient or completely physically separate and not in physical contact with the patient).

The valve 100 can be any suitable implantable prosthetic valve, such as, for example, the valve 200 described below with respect to FIGS. 2-13.

FIGS. 2-13 illustrate an embodiment of a prosthetic heart valve that can be used in conjunction with the devices and system described above and described in more detail below with respect to FIGS. 13A-16B. The prosthetic valve of FIGS. 2-13 can be delivered and deployed within a left atrium of a heart using a variety of different delivery approaches including, for example, a transapical delivery approach, a transfemoral delivery approach as described in International Application No. PCT/US15/14572 (the '572 PCT application), which is incorporated herein by reference in its entirety, or a transatrial or transjugular delivery approach as described in U.S. Patent Application Publication No. 2017/0079790 (the '790 application), which is incorporated herein by reference in its entirety.

Figure 2:
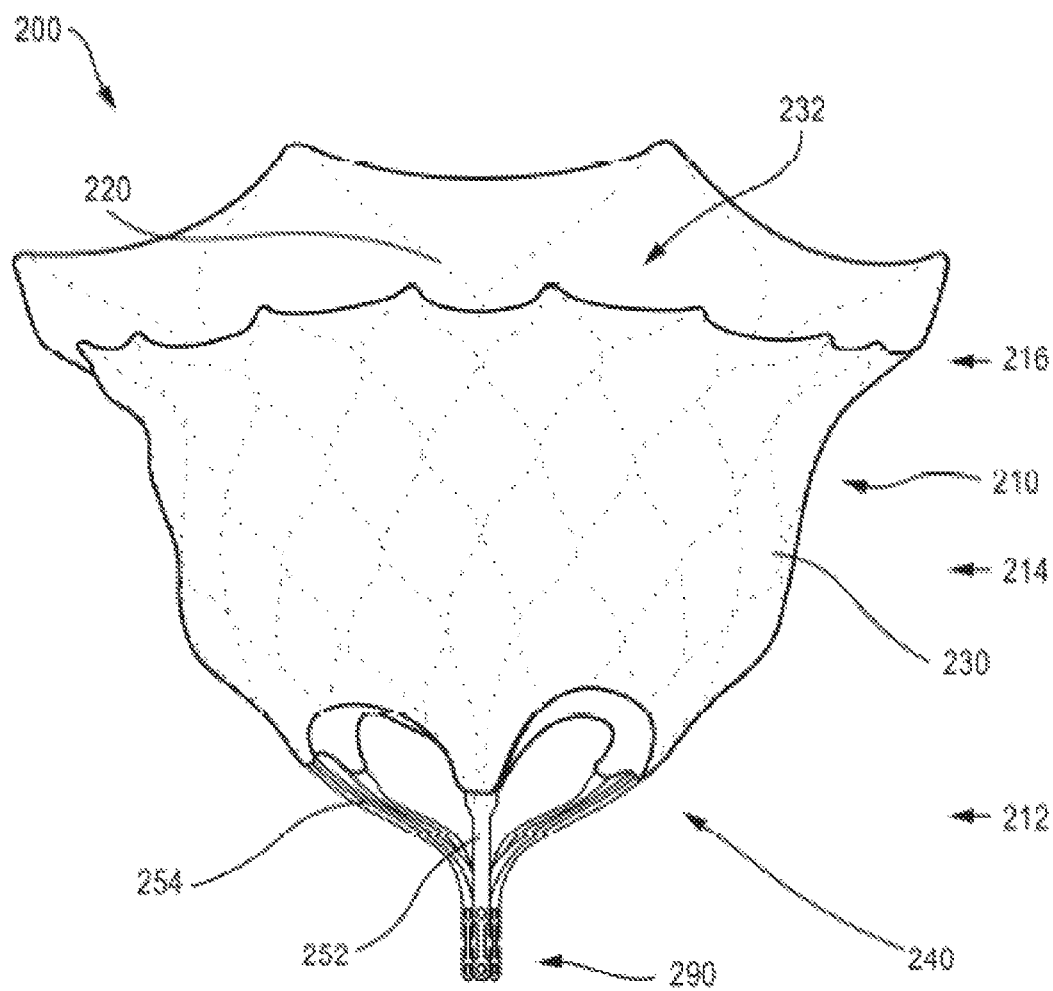
FIGS. 2-4 are front, bottom, and top views of a prosthetic heart valve according to an embodiment.
Figure 3:
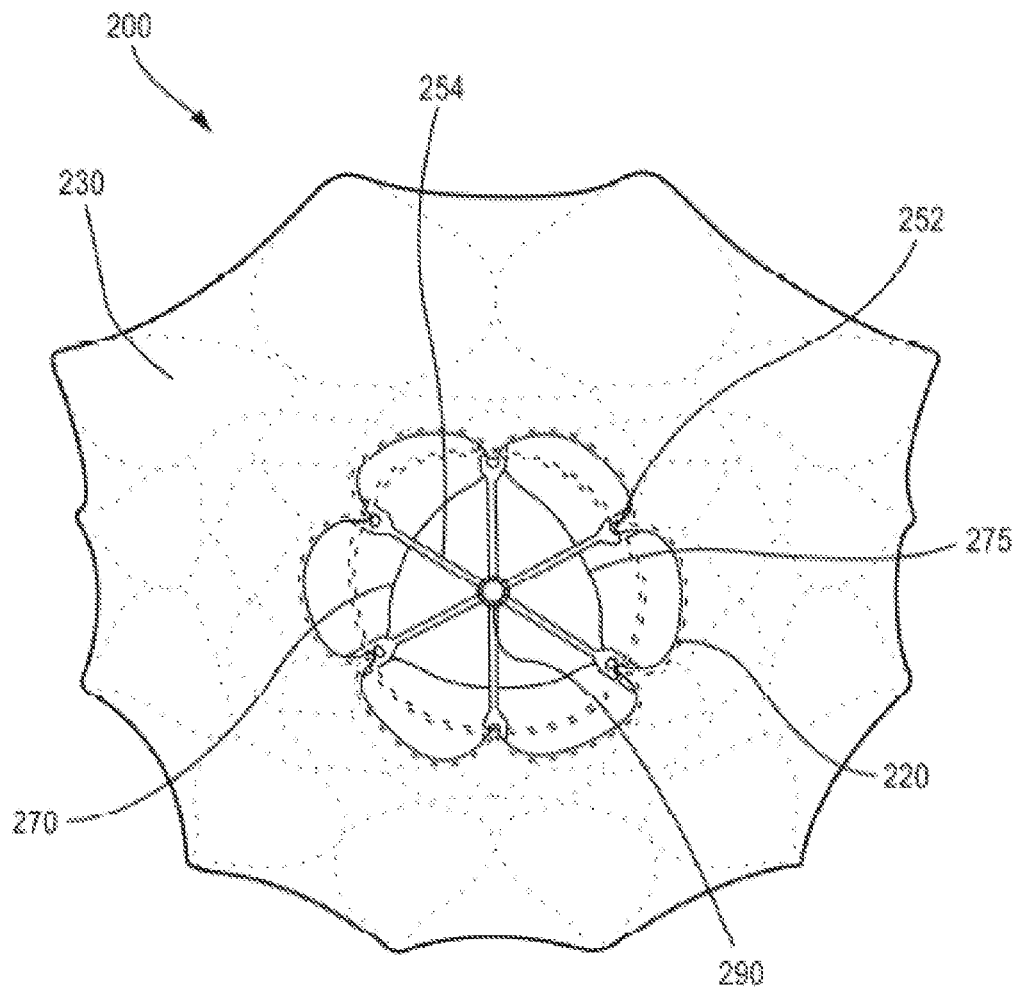
Figure 4:
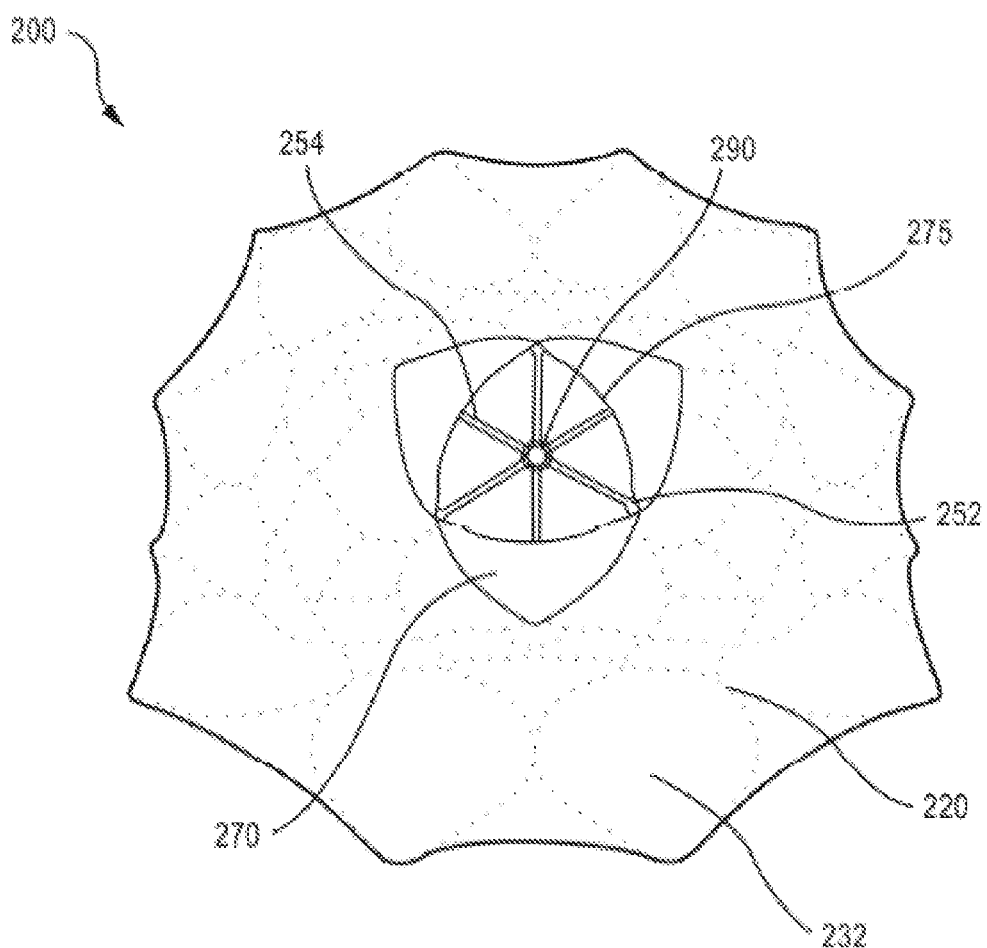

FIGS. 2-4 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 2, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 4, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering 260, and leaflets 270. As shown, the inner valve assembly 240 includes an upper portion having a periphery formed with multiple arches. The inner frame 250 includes six axial posts or frame members that support outer covering 260 and leaflets 270. Leaflets 270 are attached along three of the posts, shown as commissure posts 252 (best illustrated in FIG. 3), and outer covering 260 is attached to the other three posts, 254 (best illustrated in FIG. 3), and optionally to commissure posts 252. Each of outer covering 260 and leaflets 270 are formed of approximately rectangular sheets of material, which are joined together at their upper, or atrium end. The lower, ventricle end of outer covering 260 may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering 260 of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering 260 of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 5:
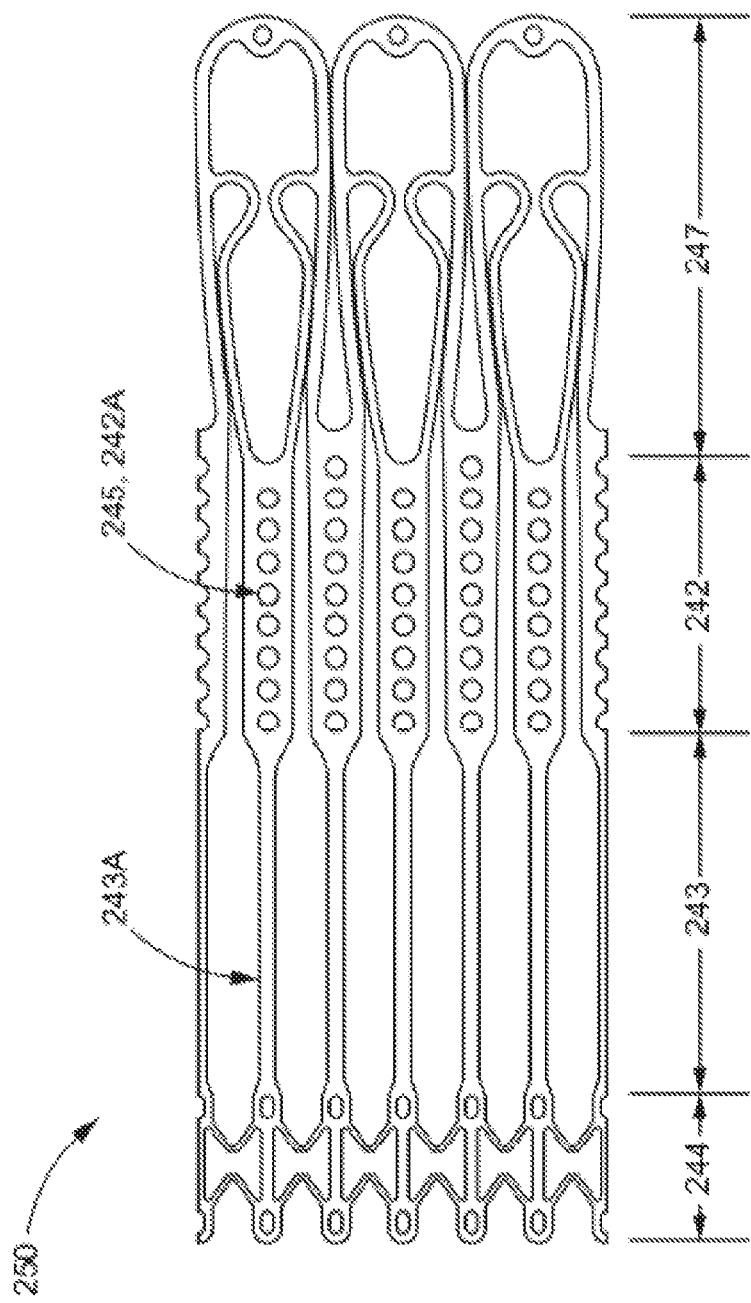
FIG. 5 is an opened and flattened view of the inner frame of the prosthetic heart valve of FIGS. 1-3, in an unexpanded configuration.
Figure 6:
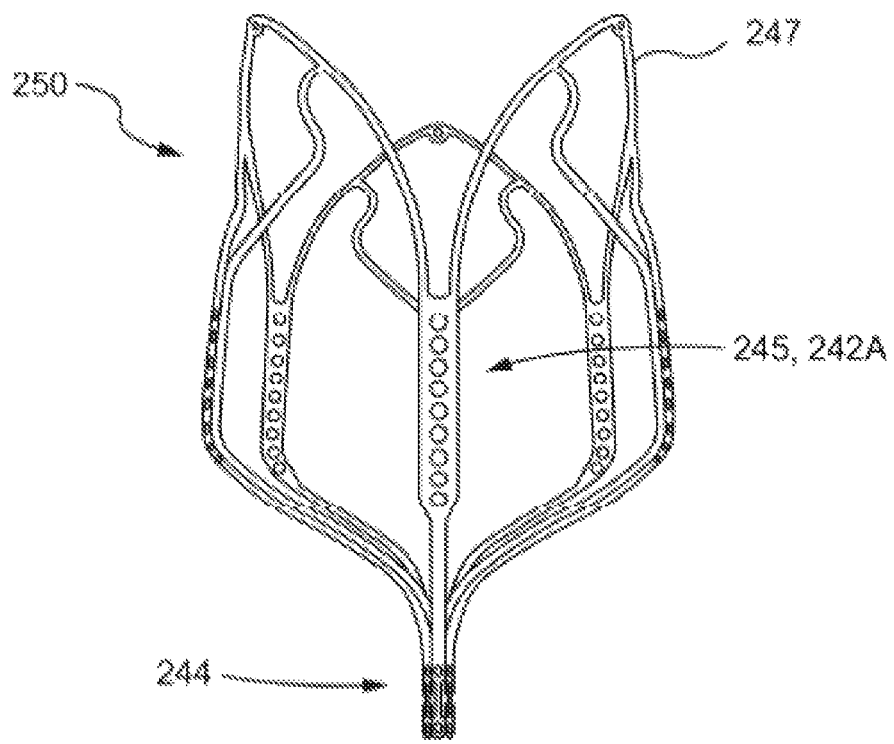
FIGS. 6 and 7 are side and bottom views, respectively, of the inner frame of FIG. 4 in an expanded configuration.
Figure 7:
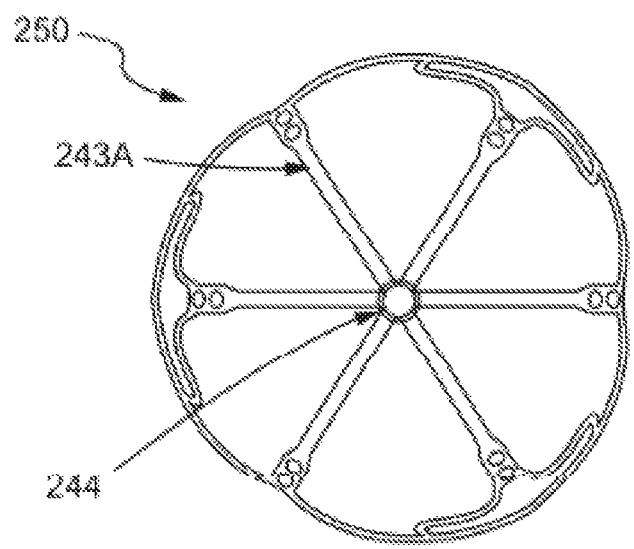

Inner frame 250 is shown in more detail in FIGS. 5-7. Specifically, FIGS. 5-7 show inner frame 250 in an undeformed, initial state (FIG. 5), a side view of the inner frame 250 in an expanded configuration (FIG. 6), and a bottom view of the inner frame 250 in the expanded configuration (FIG. 7), respectively, according to an embodiment.

In this embodiment, inner frame 250 is formed from a laser-cut tube of Nitinol®. Inner frame 250 is illustrated in FIG. 5 in an undeformed, initial state, i.e. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g. braided filament line) or onto an intermediate structure, such as a polymer or metal piece that is in turn firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 240, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed, i.e. the final, deployed configuration, in side view and bottom view in FIGS. 6 and 7, respectively.

Figure 8:
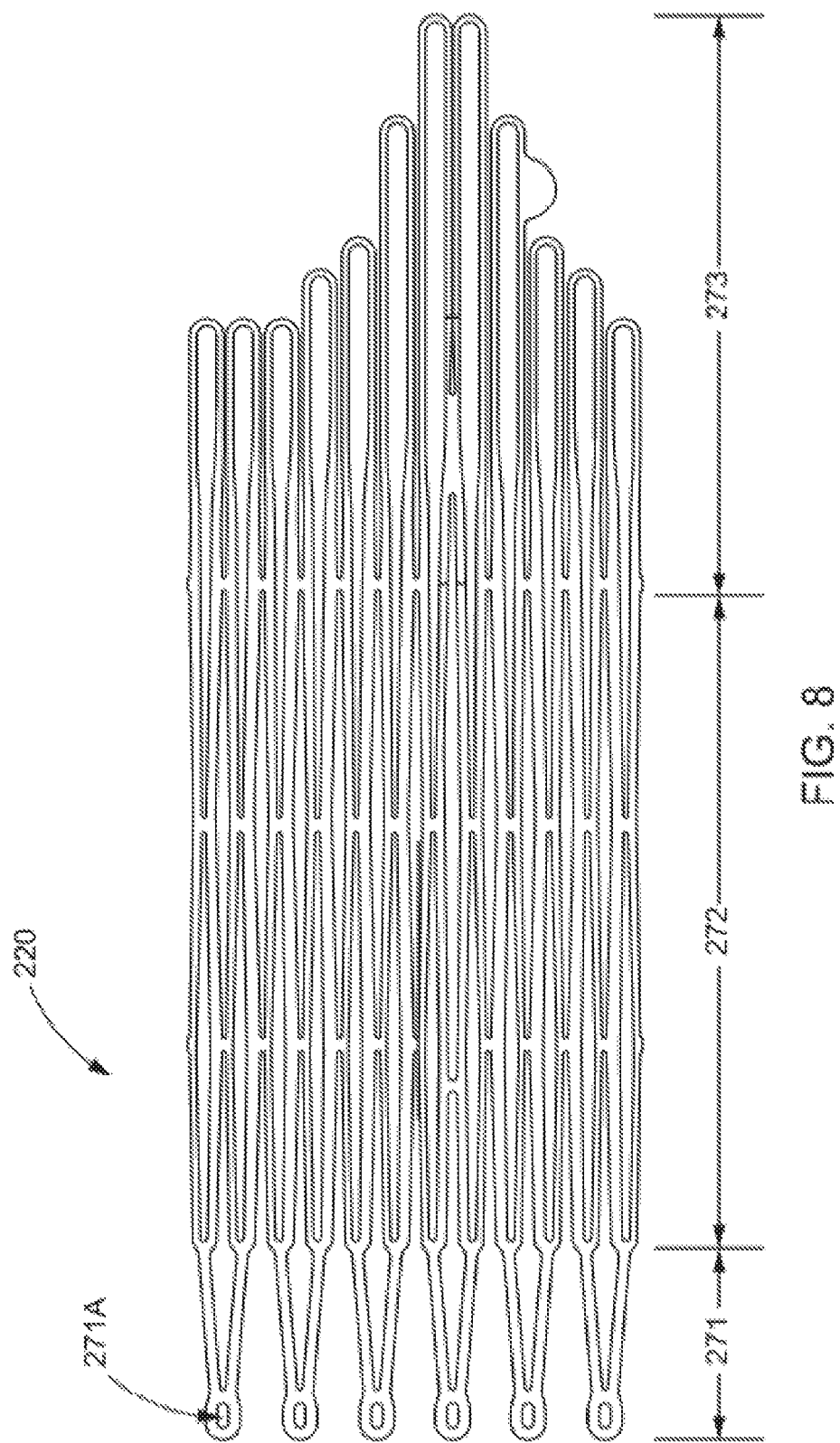
FIG. 8 is an opened and flattened view of the outer frame of the valve of FIGS. 1-3, in an unexpanded configuration.
Figure 9:
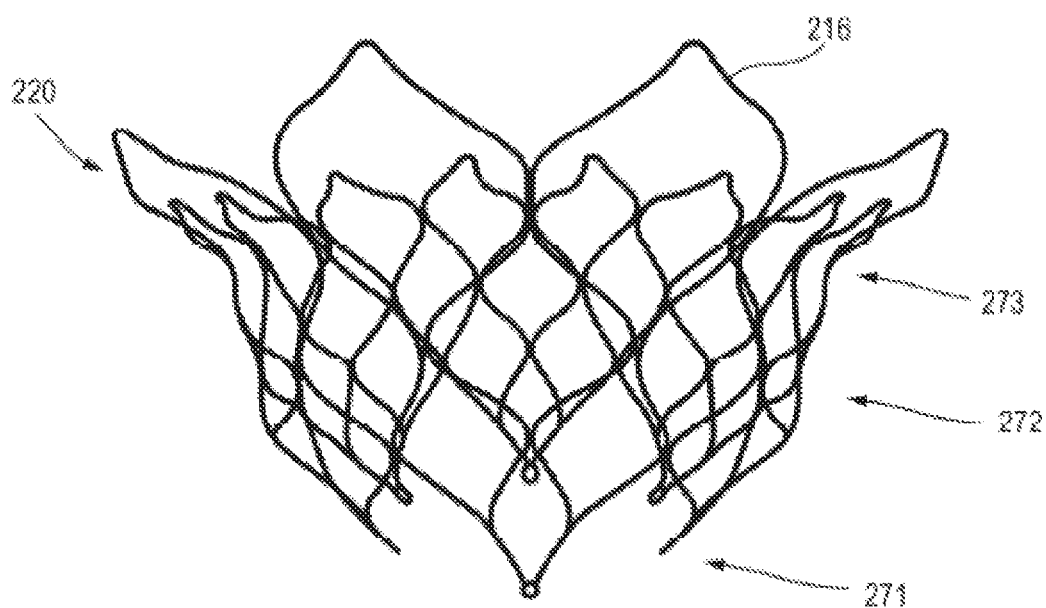
FIGS. 9 and 10 are side and top views, respectively, of the outer frame of FIG. 7 in an expanded configuration.
Figure 10:
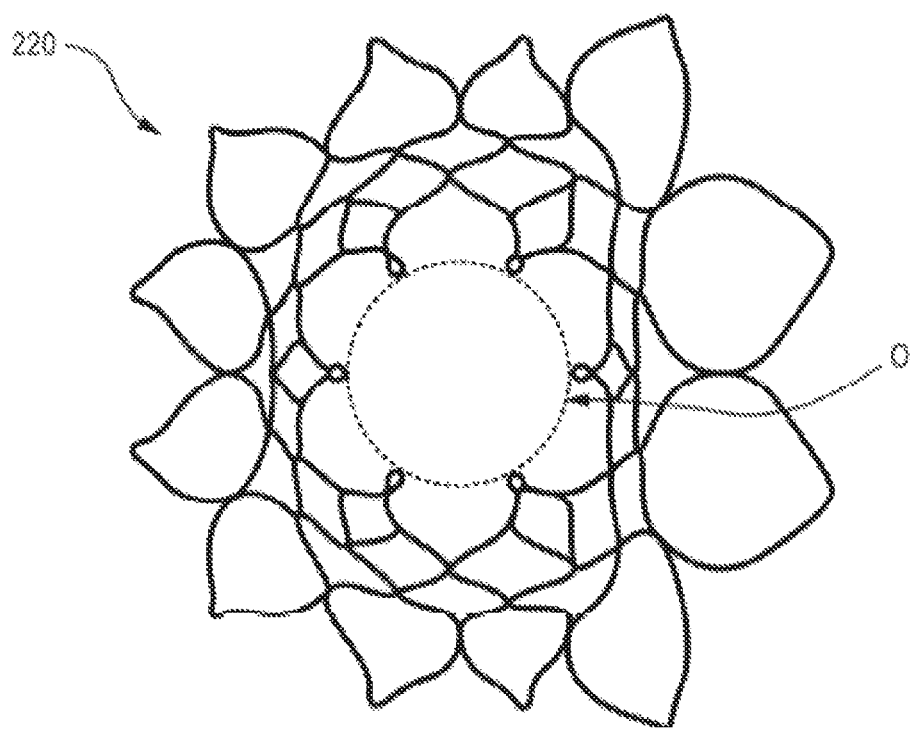

Outer frame 220 of valve 200 is shown in more detail in FIGS. 8-10. In this embodiment, outer frame 220 is also formed from a laser-cut tube of Nitinol®. Outer frame 220 is illustrated in FIG. 8 in an undeformed, initial state, i.e. as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 8. Outer frame coupling portion 271 includes multiple openings or apertures, such as 271A, by which outer frame 220 can be coupled to inner frame 250, as discussed in more detail below.

Outer frame 220 is shown in a fully deformed, i.e. the final, deployed configuration, in side view and top view in FIGS. 9 and 10, respectively. As best seen in FIG. 9, the lower end of outer frame coupling portion 271 forms a roughly circular opening (identified by "O" in FIG. 10). The diameter of this opening preferably corresponds approximately to the diameter of body portion 242 of inner frame 250, to facilitate coupling of the two components of valve 200.

Figure 11:
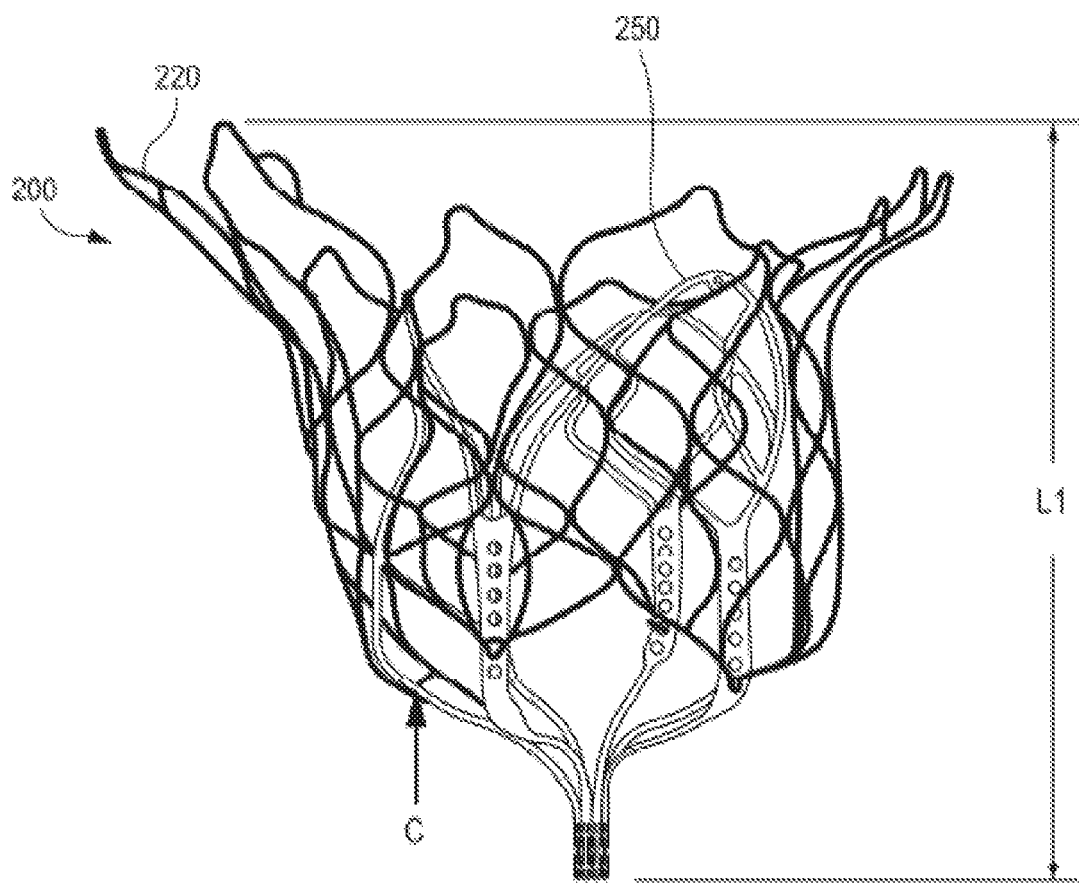
FIGS. 11-13 are side, front, and top views of an assembly of the inner frame of FIGS. 4-6 and the outer frame of FIGS. 7-9.
Figure 12:
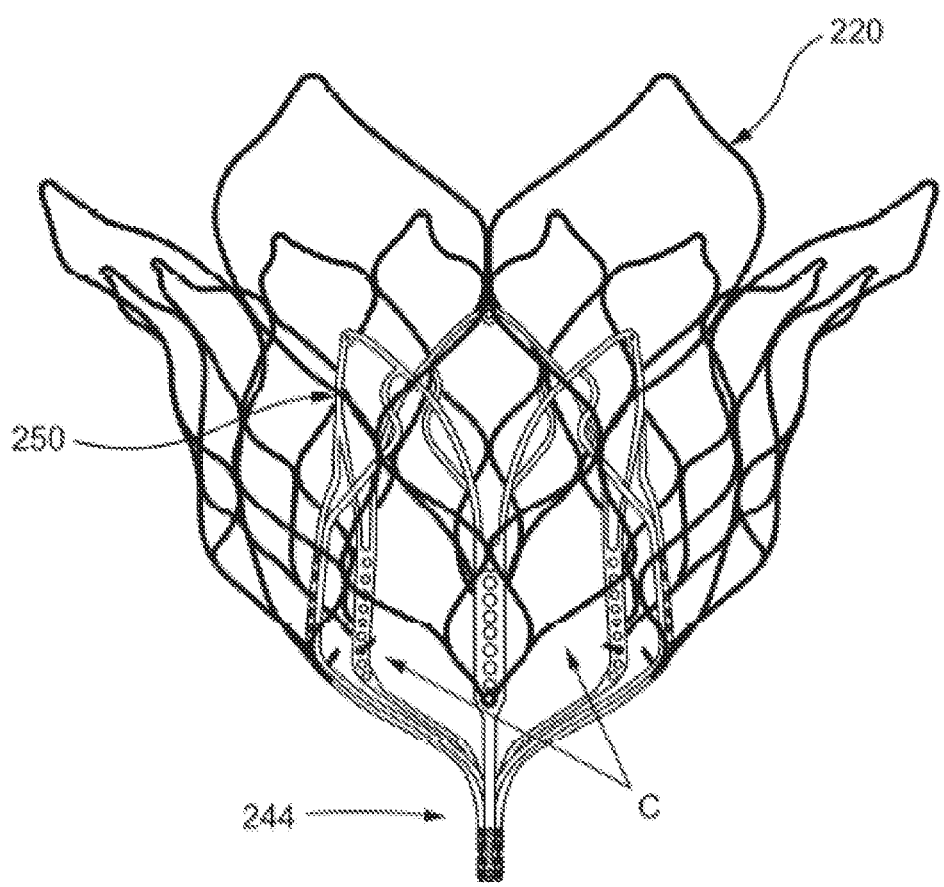
Figure 13:
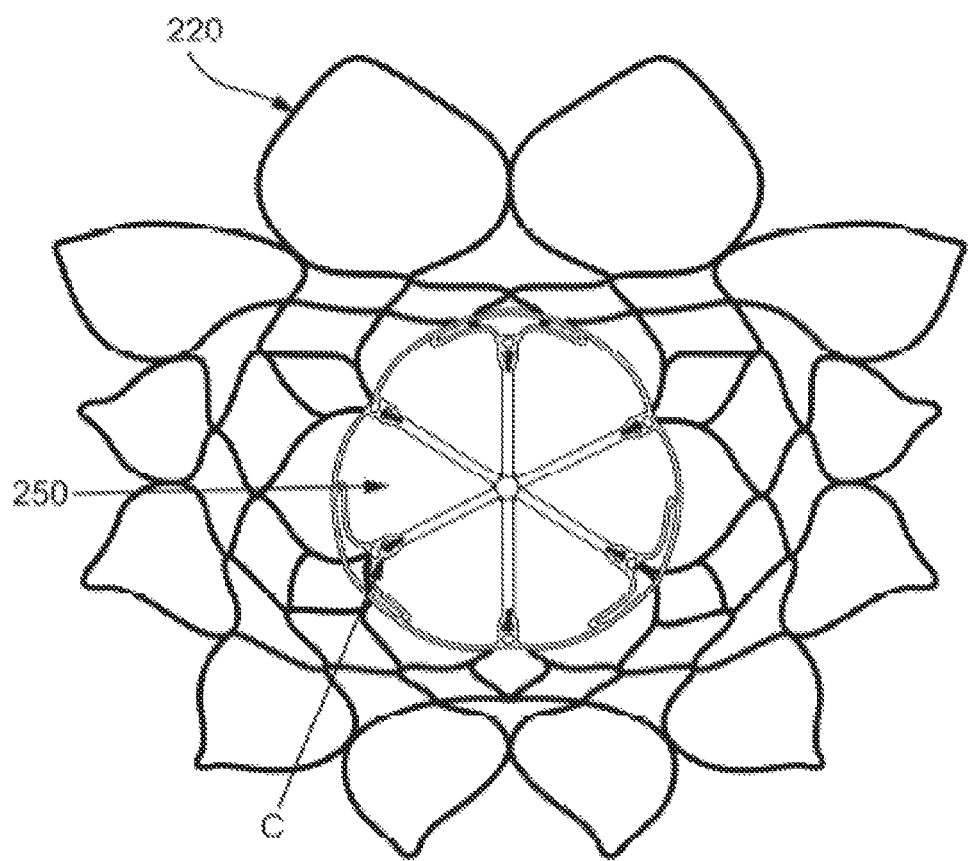

Outer frame 220 and inner frame 250 are shown coupled together in FIGS. 11-13, in front, side, and top views, respectively. The two frames collectively form a structural support for a prosthetic valve such as valve 200. The frames support the valve leaflet structure (e.g., leaflets 270) in the desired relationship to the native valve annulus, support the coverings (e.g., outer covering 230, inner covering 232, outer covering 260) for the two frames to provide a barrier to blood leakage between the atrium and ventricle, and couple to the tether (e.g., tether assembly 290) (by the inner frame 250) to aid in holding the prosthetic valve 200 in place in the native valve annulus by the tether connection to the ventricle wall. The outer frame 220 and the inner frame 250 are connected at six coupling points (representative points are identified as "C"). In this embodiment, the coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it.

As described above, various apparatus, systems and methods are described herein for pacing (e.g., selectively delivering electrical signals or stimuli) a heart to manipulate the geometry and/or function of a heart (e.g., to selectively cause ventricular contraction and/or relaxation) to limit or prevent LVOT interruption in conjunction with an implanted prosthetic valve (e.g., prosthetic mitral valve) such as, for example, the prosthetic valve 200 described above. Details regarding the various different pacing approaches are described below with reference to specific embodiments.

Figure 14A:
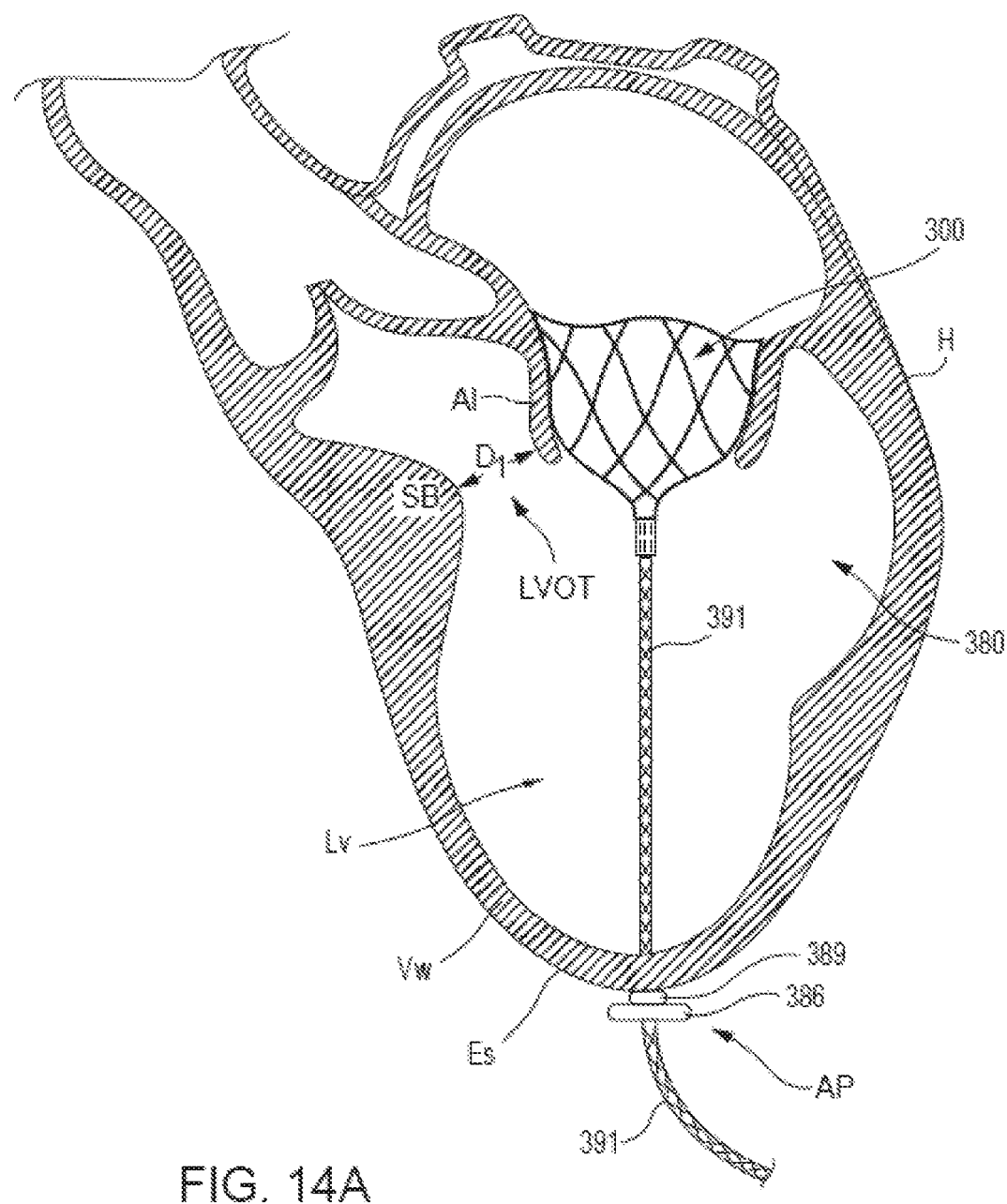
FIG. 14A illustrates in cross-sectional front view a portion of a heart having a valve-tether coupled to an electrode and implanted therein and having a pronounced septal bump, according to an embodiment.
Figure 14B:
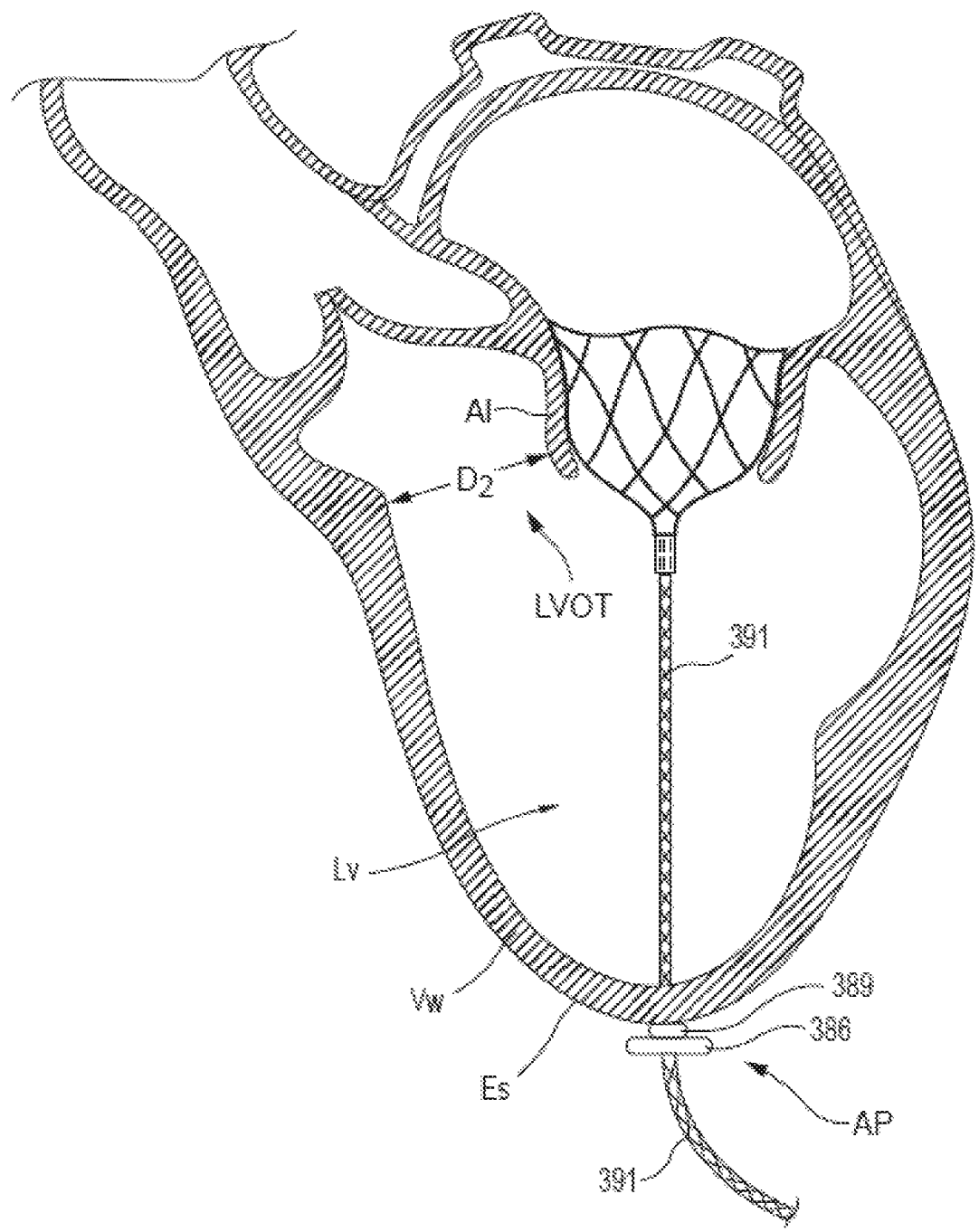
FIG. 14B illustrates in cross-sectional front view the heart and valve-tether of FIG. 14A, and showing the septal bump less pronounced.
Figure 14C:
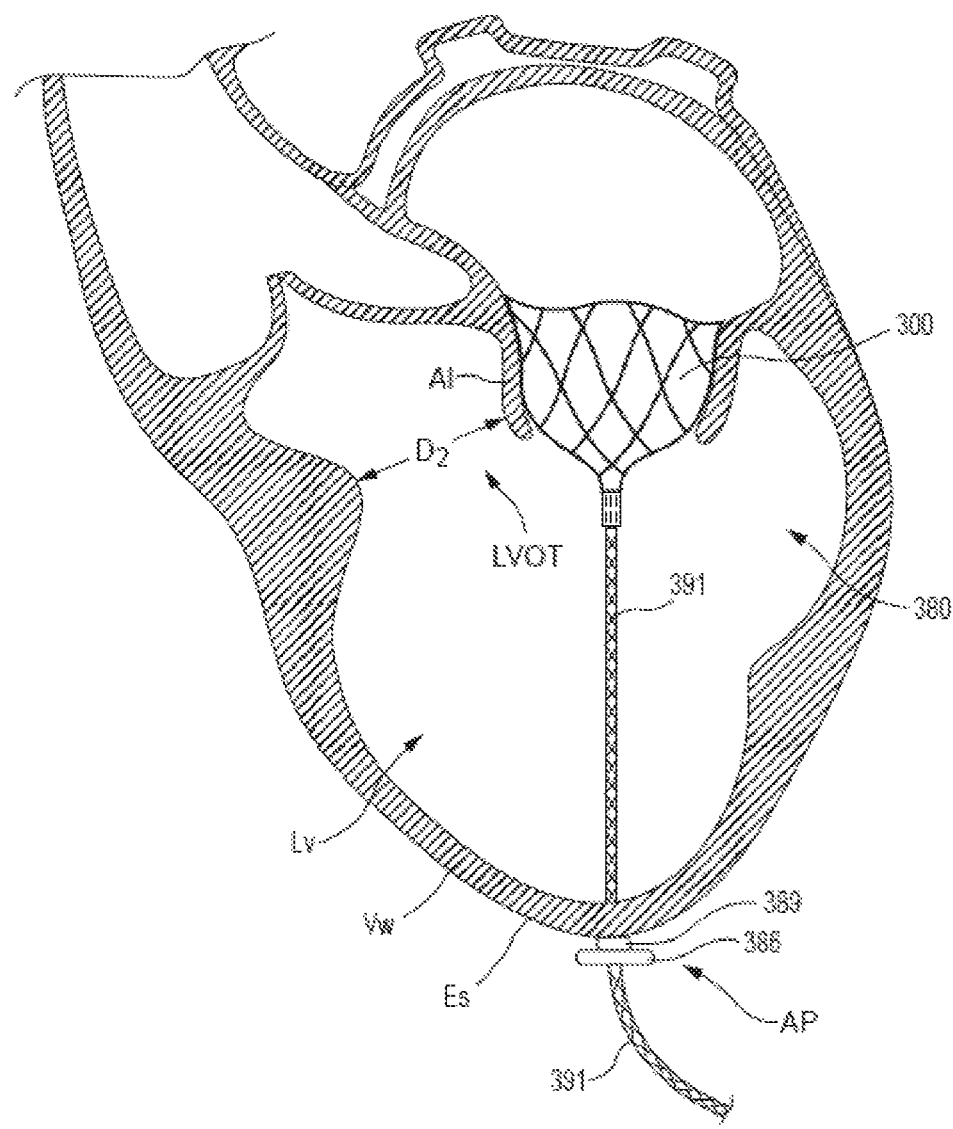
FIG. 14C illustrates in cross-sectional front view the heart and valve-tether of FIG. 14A, and showing the septal bump displaced.

In some embodiments, a method includes pacing a heart using one or more electrodes of a valve-tether that are implanted within a patient. The one or more electrodes can be placed in any suitable location along the valve-tether such that the one or more electrodes are in electrical communication with tissue (e.g., myocardial tissue) of the heart. With the one or more electrodes in electrical communication with such tissue, an electrical signal can be delivered to the tissue via the one or more electrodes. In some embodiments, for example, one or more electrodes can be disposed in contact with an inner layer of the wall of the heart (e.g., the endocardial layer). FIGS. 14A-14C illustrate in cross-sectional front view a portion of a heart H having a pronounced septal bump SB on the ventricular septum separating the left ventricle Lv from the right ventricle (not shown) and a valve 300 having a tether 391 coupled thereto and implanted therein, according to such an embodiment. In particular, FIG. 14A illustrates the heart H prior to being paced (as demonstrated by the distance D1 between the septal bump SB and the valve 300), and FIGS. 14B and 14C illustrate the heart H during or after pacing (as demonstrated by the distance D2 between the septal bump SB and the valve 300, wherein the geometry of the heart has been altered such that D2 is greater than D1). In some instances, as shown in FIG. 14B, pacing the heart H may cause a size (e.g., a thickness) and/or a shape of the septal bump BP to change to promote LVOT clearance. In other instances, in addition to or instead of altering the size and/or shape of the septal bump BP, pacing the heart H may cause the septal bump SP to be displaced (e.g., radially displaced) to promote LVOT clearance, as shown in FIG. 14C. In such instances, for example, pacing can be selectively applied to cause the septal bump SB to be displaced at a time when blood is expected or desired to flow through the LVOT.

As shown, in this embodiment, the prosthetic mitral valve 300 is deployed within the native mitral valve annulus, and the tether 391 extends proximally through the left ventricle Lv and out an opening (e.g., formed from an incision) in the ventricular wall Vw in the apex region Ap of the heart H. The tether 391 can be used to aid in both (1) holding the prosthetic valve 300 in place in the native valve annulus and (2) pacing the heart, as described in further detail herein. The prosthetic mitral valve 300 and the tether 391 are referred to herein collectively as "valve-tether 380." The prosthetic valve 300 can be constructed the same as or similar to the prosthetic valve 200, described above, and can function in a similar manner. Thus, some details regarding the valve 300 are not described below. It should be understood that for features and functions not specifically discussed, those features and functions can be the same as or similar to the valve 200. Further, it should be understood that the systems described herein can include other valve configurations couplable or coupled to a tether.

As shown in FIGS. 14A and 14B, an apical pad 386 is coupled to a proximal end portion of the tether 391 and can be used to secure the tether 391 and the valve 300 in a desired position and orientation within the heart. The apical pad 386 can be constructed the same as or similar to and can function in the same or similar manner as any of the apical pads described in U.S. Patent Application Publication No. 2016/0143736 (the '736 application) and/or U.S. Patent Application Publication No. 2016/0367368 (the '368 application), both of which are incorporated by reference herein in their entireties. Thus, some details regarding the apical pad 386 are not described below. It should be understood that for features and functions not specifically discussed, those features and functions can be the same as or similar to any of the apical pads described herein, in the '736 application, and/or the '368 application.

With the valve 300 deployed within the mitral valve annulus and the tether 391 extending outside of the heart, as shown, the tether 391 can be threaded through an opening of the epicardial pad 386, and the epicardial pad 386 can be moved into a desired position on or near the apex Ap of the heart H. In some instances, prior to moving the epicardial pad 391 into position on the apex Ap of the heart H, conventional purse string sutures can be used to close the incision in the heart H through which the tether 391 extends.

Further as shown, in this embodiment, an electrode 389 is coupled to a proximal end portion of the tether 391 and is in contact with the ventricular wall Vw of the heart H such that an electrical signal (not shown) can be conveyed from the electrode 389 to the heart H to pace the heart H, and cause the septal bump SB to retract or reconfigure and the LVOT to increase. For example, the electrodes 389 can be operatively coupled to an pulse generator (not shown) which can provide energy to the electrodes 389. In some embodiments, the electrodes are coupled to the pulse generator via a lead wire(s) and in some embodiments, the tether 391 can be used to operatively couple the electrodes 389 to the pulse generator as described in more detail below. Prior to such pacing, as discussed above, a heart H with a pronounced septal bump SB as shown in FIG. 14A can contribute to LVOT interruption, as illustrated in FIG. 14A by the abnormally small distance D1 between the boundary through which the LVOT is defined, e.g., between (a) the portion of the ventricular wall Vw at which the septal bump SB is located and (b) the anterior leaflet A1 of the native mitral valve. During pacing of the heart H via the valve-tether 391, however, a proper LVOT can be created and/or sustained (i.e., LVOT interruption can be inhibited or reduced during systole) by increasing the distance between the boundary through which the LVOT is defined, e.g., between (a) the portion of the ventricular wall Vw at which the septal bump SB is located and (b) the anterior leaflet A1 of the native mitral valve, as illustrated by distance D2 in FIG. 14B. Note that although in FIGS. 14A and 14B a gap is illustrated between the upper surface of the apical pad 396 and the epicardial surface Es of the heart H, the apical pad 396 and the electrode 389 can be configured such that both the apical pad 396 is in contact with or is substantially flush with the epicardial surface Es and the electrode 389 is in contact with the ventricle wall Vw (e.g., the epicardial surface Es, intraventricular wall, etc.). For example, in some embodiments, the electrode may be embedded within and/or a part of the apical pad.

Although in this embodiment a single electrode 391 is disposed between the apical pad 386 and the epicardial surface Es of the heart H, in other embodiments any suitable number of electrodes can be used to pace and/or multi-pace the heart, and those electrodes can be disposed in any suitable locations within and about the heart H (e.g., at an inner surface or outer surface of the heart wall, within the heart wall in the myocardium, in the ventricle, in the atrium, and/or the like). In some embodiments, for example, a first electrode can be placed in contact with the heart near the apex region of the heart (similar to as discussed above with respect to electrode 389), and a second electrode can be placed in contact with the heart somewhere along the tether within the ventricle and/or at or near the implanted prosthetic mitral valve. In this manner, the heart can be paced substantially simultaneously from multiple locations. In some instances, it may be desirable to pace the atrium of the heart. In such instances, for example, one or more electrodes could be coupled to an upper portion of the prosthetic mitral valve, e.g., coupled to a cuff portion of the prosthetic mitral valve such that when the cuff portion is seated on the native valve annulus the one or more electrodes coupled thereto can convey electrical signals to the atrium and/or annular region of the native valve.

Various factors can be considered to determine the number and placement of electrodes that may be needed. For example, the size and geometry of the heart (and particularly the ventricle) varies across patients, and to ensure sufficient contact between at least one electrode and heart tissue for pacing, the size and geometry of the heart can be factored into selecting a number of electrodes and locations at which those electrodes are disposed. In some embodiments, for example, an electrode can be disposed at or on an upper surface of the apical pad such that, with the prosthetic valve implanted and the tether extended across the ventricle therefrom, and through an opening in the apex region of the heart, the apical pad can be slid towards the apex region of the heart along the tether until the electrode physically contacts the epicardial surface of the heart. In such an embodiment, the electrode can be coupled to the apical pad in any suitable manner. For example, in some instances, the electrode can be soldered to the upper surface of the apical pad. In other instances, the upper surface of the apical pad can include an electrode. In either instance, similar to the apical pad, the electrode can include a lumen through which the tether can be routed such that the electrode can be slid along the tether and into contact with the heart.

Figure 15:
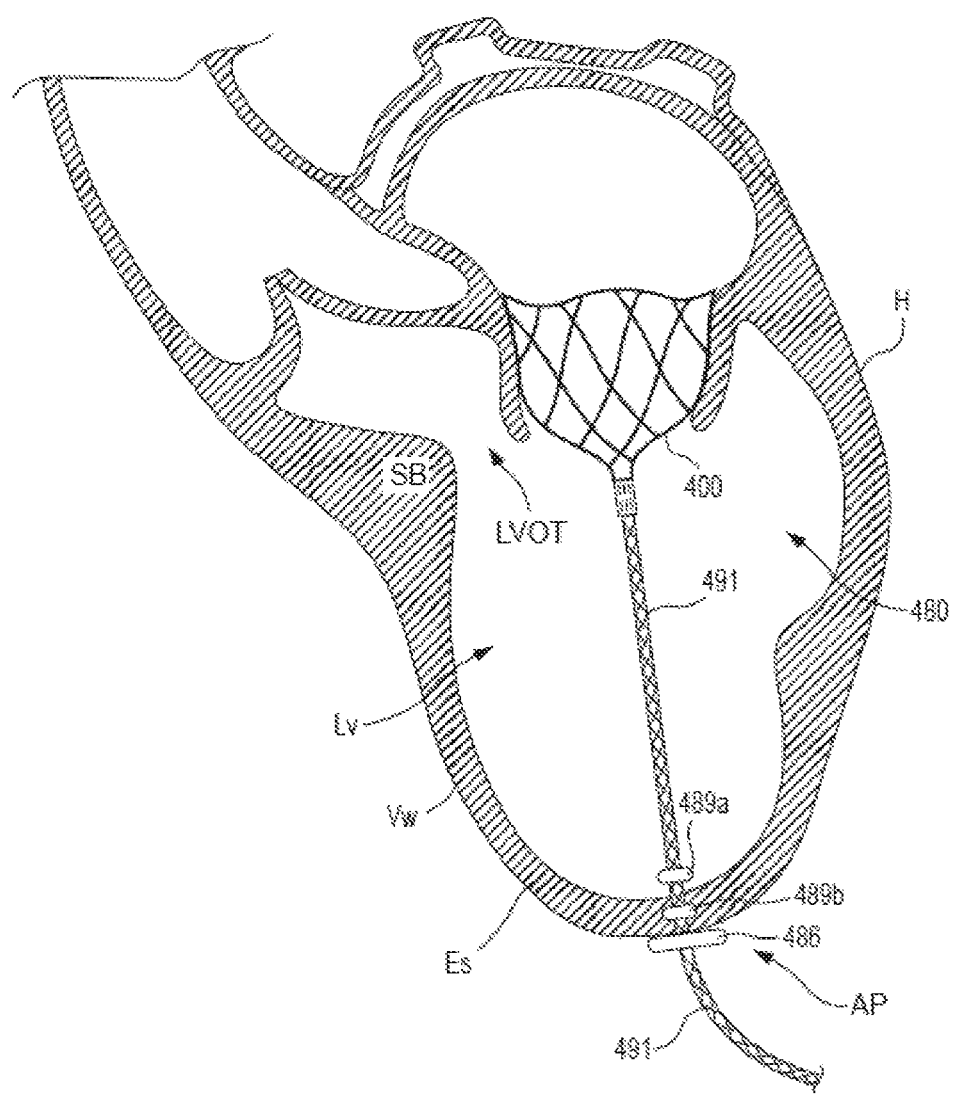
FIG. 15 illustrates in cross-sectional front view a portion of a heart having a valve-tether with multiple electrodes implanted therein, according to an embodiment.

In yet further embodiments, to accommodate for various ventricle sizes and geometries, multiple electrodes can be placed along portions of the tether expected to contact the heart wall, e.g., the myocardium of the heart near its apex region. For example, a valve-tether can have multiple electrodes placed along its tether at or near a portion or zone of the tether expected to extend through the opening in the apex region of the heart for anchoring of the prosthetic mitral valve, as discussed above with respect to valve 300, to ensure that at least one of the electrodes from the multiple electrodes is in sufficient contact with the heart for pacing. Such an embodiment is illustrated in FIG. 15. Identifying and/or confirming sufficient contact between at least one of the electrodes and the heart for pacing can be accomplished, for example, by trial and error. In such instances, signals can be conveyed via multiple electrodes while imaging the heart to detect if pacing has occurred. Additionally or alternatively, identifying and/or confirming sufficient contact between at least one of the electrodes and the heart for pacing can be accomplished, for example, by retrieving and analyzing one or more signals (e.g., an electrical impedance signal) received from one or more electrodes, as described in connection with additional embodiments described below.

FIG. 15 illustrates in cross-sectional front view a portion of a heart H having a pronounced septal bump SB and a valve-tether 480 (comprised of valve 400 and tether 491) implanted therein, according to an embodiment. The valve-tether 480 can be constructed the same as or similar to the prosthetic valve 200 and/or valve-tether 380, described above, and can function in a similar manner. Thus, some details regarding the valve-tether 480 are not described below. It should be understood that for features and functions not specifically discussed, those features and functions can be the same as or similar to the valve 200 and/or the valve-tether 380. In this embodiment, two electrodes, i.e., a first electrode 489a and a second electrode 489b, are disposed on or about the tether 491 near the apex region Ap of the heart H when the valve 400 is deployed within the native annulus and the tether 491 extends therefrom, through the left ventricle Lv, and out the ventricle wall Vw, and then anchored via the apical pad 496. The apical pad 496 can be constructed the same as or similar to the apical pad 396, described above, and can function in a similar manner. Thus, some details regarding the apical pad 496 are not described below. It should be understood that for features and functions not specifically discussed, those features and functions can be the same as or similar to the apical pad 496.

As shown, with the valve-tether 480 implanted within the heart H, the second electrode 489b is in physical contact with the ventricle wall Vw (e.g., the myocardium) and is thus in a suitable position for pacing the heart H, whereas the first electrode 489a is disposed in the ventricle and not in physical contact with the ventricle wall Vw or any other heart tissue, and is thus not in a suitable position for pacing the heart H. Note that this arrangement is for illustrative purposes, but in practice, the first electrode 489a in such an arrangement may be in contact with heart tissue within the ventricle, such as, for example, a papillary muscle (not shown) near the apex region Ap of the heart.

By distributing multiple electrodes (e.g., first electrode 489a and second electrode 489b) along the tether 491 in this manner provides for suitable pacing capabilities for patients having various sized and shaped hearts. For example, if the valve-tether 480 were implanted in a patient having a ventricle with a greater distance between the native annulus and the apex region of the heart (e.g., a longer or taller ventricle), a greater length of the tether 491 would extend from the valve 400 through the ventricle, and as a result, the first electrode 489a may be disposed in contact with the ventricle wall Vw (e.g., in the position of the second electrode 489b shown in FIG. 15) and thus in a suitable position for pacing the heart H, and the second electrode 489b may extend outside and not in physical contact with heart not be in physical contact with the ventricle wall Vw, and thus not in a suitable position for pacing the heart H.

Although in this embodiment only two electrodes are coupled to the tether 491, in other embodiments, any suitable number of electrodes can be used to pace the heart H. For example, in some embodiments, more than two electrodes (e.g., 3, 4, 5, 6 or more) can be coupled to the tether in an effort to have a suitable number of electrodes contact the heart H for pacing when implanted therein, similar to as described above with respect to the valve tether 480. The number of electrodes used and/or the placement of the electrodes along the tether may be, for example, based on a particular patient's heart size and geometry, and/or an average heart size and geometry of similar patients. For example, in some embodiments, the electrodes may be placed within about 5 mm to about 70 mm from the distal end portion of the tether (i.e., the portion of the tether that is coupled to the implanted prosthetic valve) such that one or more of the electrodes is in suitable contact with the ventricle wall of the heart. The distance or range can be selected, for example, based on a patient's anatomy. In instances in which a patient has a dilated anatomy, for example, a suitable distance may be at a higher end of the example range of about 5 mm to about 70 mm. In instances in which a patient does not have a dilated anatomy and/or is a smaller or younger patient, perhaps a placement of the electrodes would be placed close to the lower end of the example range of about 5 mm to about 70 mm. Further, the electrodes can be spaced from each other by a distance suitable to ensure at least one electrode is disposed is sufficient contact with the heart after implantation. In some embodiments, for example, two or more electrodes can be coupled to tether and spaced apart by a distance of about 5 mm to about 15 mm, such that at least one or more of the electrodes when implanted is disposed in contact with heart tissue (e.g., within the incision formed in the myocardium through which the tether extends). In some instances, the tether can be adjusted and/or tensioned to bring one or more of the electrodes into contact with heart tissue, such as the myocardium.

In addition to or instead of implanting a valve-tether with one or more electrodes for pacing purposes, an implanted valve-tether can include one or more sensors and/or electrodes for sensing and/or measuring various characteristics of the heart. In this manner, the valve-tether itself, as opposed to, for example, a separate diagnostic or measurement device or medical procedure, can provide for monitoring of the heart's post-implantation response to the implant in a non or minimally invasive manner. Such an embodiment is illustrated in FIG. 16.

Figure 16:
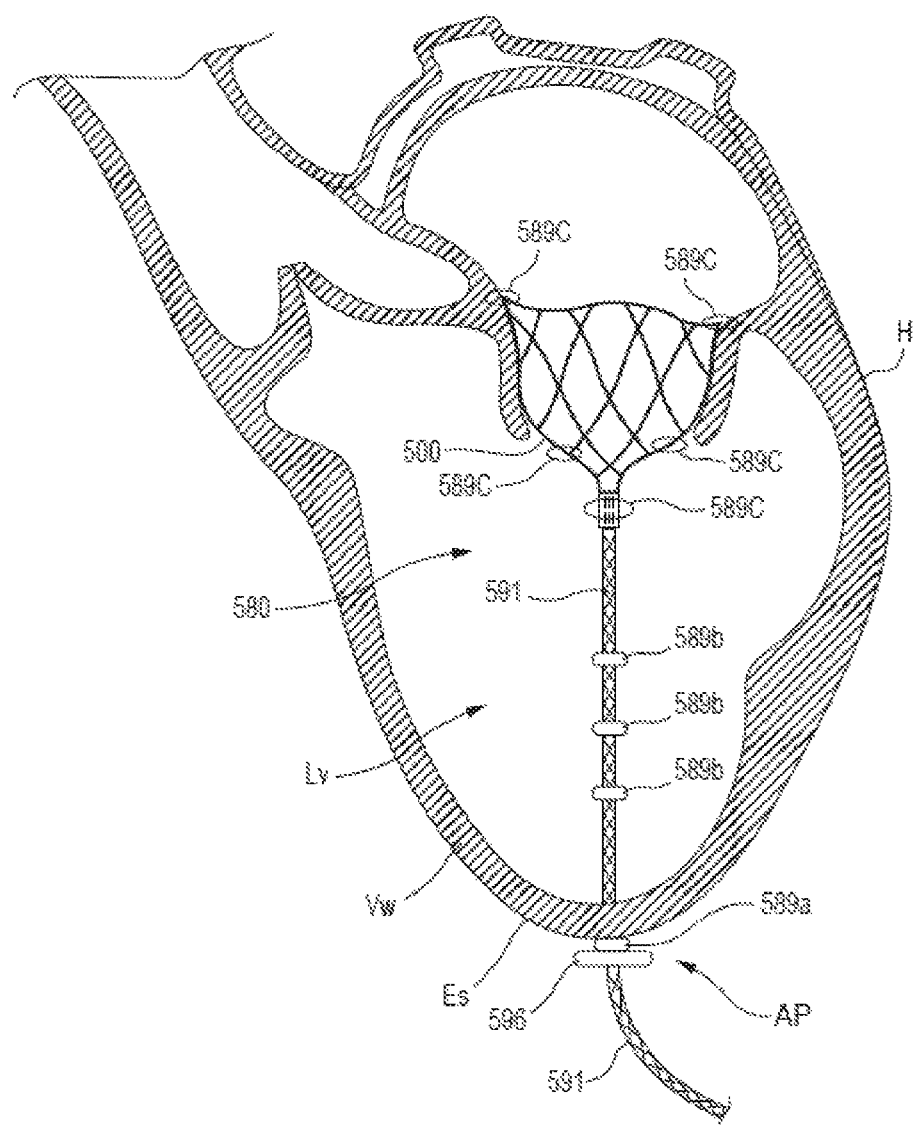
FIG. 16 illustrates in cross-sectional front view a portion of a heart having a valve tether implanted therein and with multiple electrodes distributed thereon, according to an embodiment.

FIG. 16 illustrates in cross-sectional front view a portion of a heart H having a valve-tether 580 (comprised of valve 500 and tether 591) anchored within the heart H using an apical pad 496 and having multiple electrodes 589 distributed thereabout. The electrodes 589 in this embodiment are configured for sensing signals within the heart H for measurement and diagnostic purposes, but it should understood that in alternative embodiments one or more of the electrodes 589 could be used to pace the heart, similar to as described above with respect to previous embodiments. In such embodiments, for example, one or more electrodes can be used for pacing while one or more electrodes can be used for measuring and/or diagnostics. For ease of explanation and illustration, in this embodiment, the electrodes 589 are shown and described as including an apex electrode 589a, ventricle electrodes 589b, and prosthetic valve electrodes 589c to identify the particular regions of the heart H in which the electrodes 589 are located and the associated data to be sensed by those electrodes 589, as described in further detail below.

The valve-tether 580 can be constructed the same as or similar to the prosthetic valve 200, the valve-tether 380, and/or the valve-tether 480, described above, and can function in a similar manner. Thus, some details regarding the valve-tether 580 are not described below. It should be understood that for features and functions not specifically discussed, those features and functions can be the same as or similar to the valve 200, the valve-tether 380, and/or the valve-tether 480. Similarly, the apical pad 596 can be constructed the same as or similar to the apical pads described above, e.g., the apical pad 396 and/or the apical pad 496, and can function in a similar manner. Thus, some details regarding the apical pad 596 are not described below. It should be understood that for features and functions not specifically discussed, those features and functions can be the same as or similar to the apical pad 396 and/or the apical pad 496.

As illustrated in FIG. 16, the electrodes 589 may be disposed about or distributed along the valve-tether 580 in various locations in which desirable heart-related measurements could be sensed, as described in more detail herein. It should be understood, however, that while the electrodes 589 are illustrated in FIG. 16 in particular locations, in other embodiments, any suitable amount of electrodes may be distributed in any suitable manner along the valve-tether 580 and/or the apical pad 589. In this embodiment, for example, the apex electrode 589a is disposed about the tether 591 and in contact with the epicardial surface Es of the ventricular wall Vw of the heart H. Although the apex electrode 589a is shown disposed between the epicardial surface Es and the apical pad 591, in other embodiments, the apex electrode 589a can be disposed in any suitable location within the apex region Ap of the heart H, e.g., embedded at least partially within the apical pad 596 and/or disposed along the tether 591 and within the opening formed in the ventricle wall Vw through which the tether 591 extends from the ventricle V to outside the heart H. In addition to sensing signals generated by and/or within the heart H, the apex electrode 589a can be used to deliver pulse(s) to pace the heart, as described above with respect to previous embodiments.

Whether delivering electrical signals to pace the heart or measuring or analyzing signals received from the heart, those signals can be delivered to and/or retrieved from the implanted electrodes in any suitable manner. For example, one or more lead wires can extend from the one or more electrodes to outside the heart and then couple to an implanted pulse generator, such as, a pacemaker, a cardioverter defibrillator, and/or a similar pulse generator configured to generate electrical pulses and/or process electrical signals sensed by the electrodes. Details regarding various approaches are described below with reference to specific embodiments.

In some embodiments, for example, an implanted valve-tether similar to or the same as the valve-tethers described above can include one or more lead wires (also referred to herein as "lead" or "electrode lead") extending from one or more electrodes (e.g., apical electrodes, ventricle electrodes, and/or prosthetic valve electrodes) through a lumen defined by the tether, to outside the heart, and then coupled to an implanted pulse generator. FIG. 17 illustrates such an embodiment.

Figures 17A, 17B:
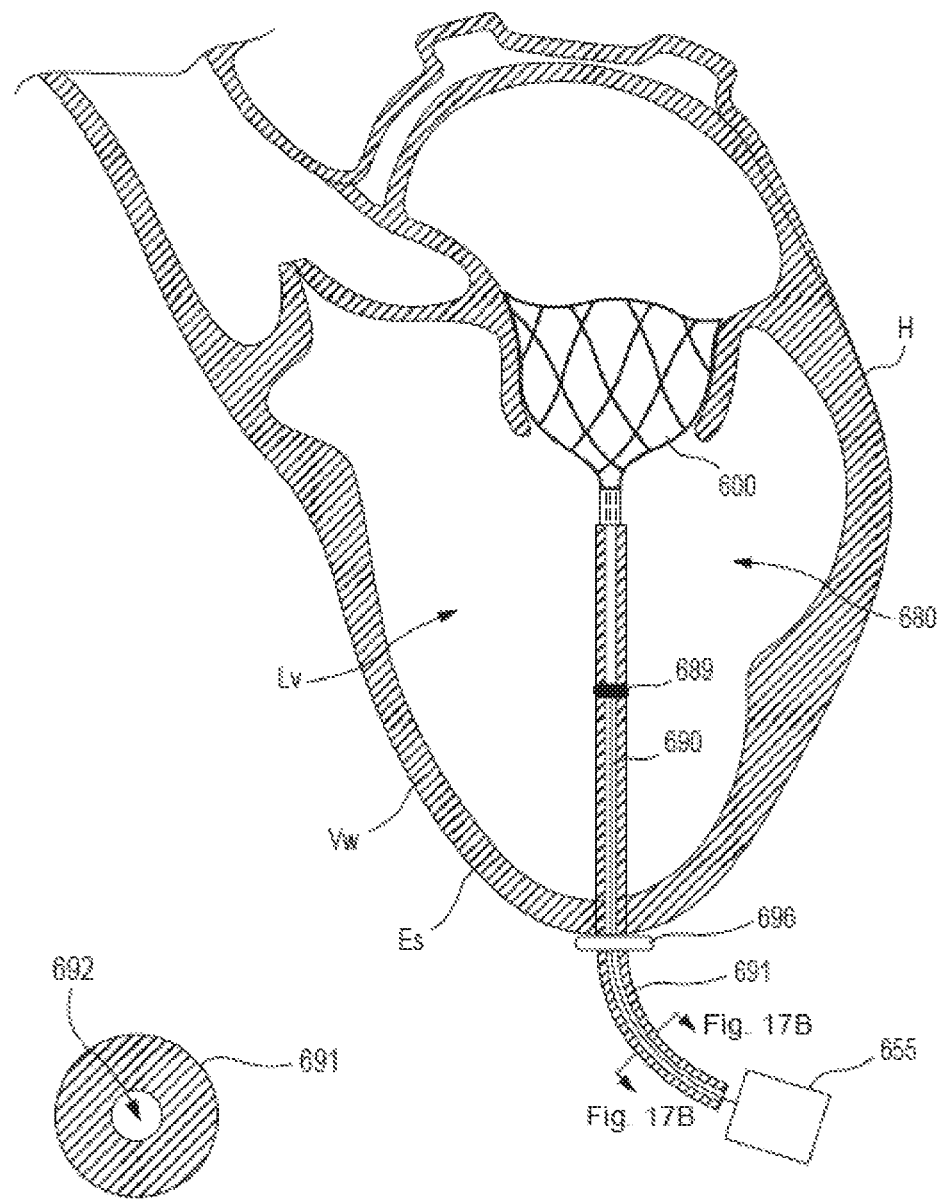
FIG. 17A illustrates in cross-sectional front view a portion of a heart having a valve-tether implanted therein, with an electrode lead disposed within a lumen of the tether, according to an embodiment.
FIG. 17B illustrates a cross-sectional view of the tether of FIG. 17A.

FIG. 17A illustrates in cross-sectional front view a portion of a heart H having a valve-tether 680 (comprised of valve 600 and tether 691) implanted therein, with the tether 691 also shown in cross-section and defining a lumen 692 through which an electrode lead 690 extends from an electrode 689 to an implanted pulse generator outside the heart, according to an embodiment. FIG. 17B illustrates an end view of the tether 691 with the lumen 692 defined therethrough. The valve-tether 680 can be constructed the same as or similar to the prosthetic valve 200 and/or any of the valve-tethers described herein, and can function in a similar manner. Thus, some details regarding the valve-tether 680 are not described below. It should be understood that for features and functions not specifically discussed, those features and functions can be the same as or similar to the valve 200 and/or the valve-tethers described herein with respect to other embodiments. Similarly, the apical pad 696 can be constructed the same as or similar to the apical pads described herein with respect to other embodiments. Thus, some details regarding the apical pad 696 are not described below. It should be understood that for features and functions not specifically discussed, those features and functions can be the same as or similar to any of the apical pads described herein.

For ease of explanation and illustration, in this embodiment, only a single electrode 689 and a single electrode lead 690 are shown and described, however, it should be understood that in other embodiments, such as the embodiments described above, any suitable number of electrodes and electrode leads can be implanted with the valve-tether, and in any suitable location (e.g., in the atrium, ventricle, within the heart wall, outside and in contact with the heart wall, and/or the like). In instances in which multiple electrodes and leads are implanted, electrode leads extending from those electrodes can share a common lumen through the tether and/or can be routed or threaded through multiple separate lumens defined by the tether.

As shown, with the valve-tether 680 implanted within the heart H and anchored to the heart H using the apical pad 696, the electrode lead 690 extends from the electrode 689 through the lumen 692 of the tether 691 from within the left ventricle Lv, through the opening in the ventricle wall Vw, outside the heart H, and is then coupled to a pulse generator 655. The tether 689 can define one or more side apertures through which the electrode lead can enter from the electrode 689 and into the lumen 692 of the tether 691. In some instances, for example, the tether 689 can be a braided tether, and the electrode lead 690 can extend from the electrode 689 through gaps or apertures between braids in the tether 689 and into the lumen 692 of the tether 691.

The pulse generator 655 can be any suitable device configured to generate and deliver electrical signals and process the same. The pulse generator 655, for example, can be a pacemaker, a cardioverter defibrillator, and/or the like.

In some instances, for example, the pulse generator 655 can include a battery coupled to a computerized electrical signal generator that is configured to be coupled to the electrode lead 690. Further, in some instances, the pulse generator 655 can include wireless communication technology, such as a radio configured to receive and/or transmit data, e.g., transmit sensor data acquired from the electrode 689. Some non-limiting examples of pulse generators includes the Proclaim™ Elite Recharge-free SCS System, the Prodigy MRI™ Implantable Pulse Generator, and the Pulse Generator Dual-Chamber (DDD), model 3085.

Figure 18:
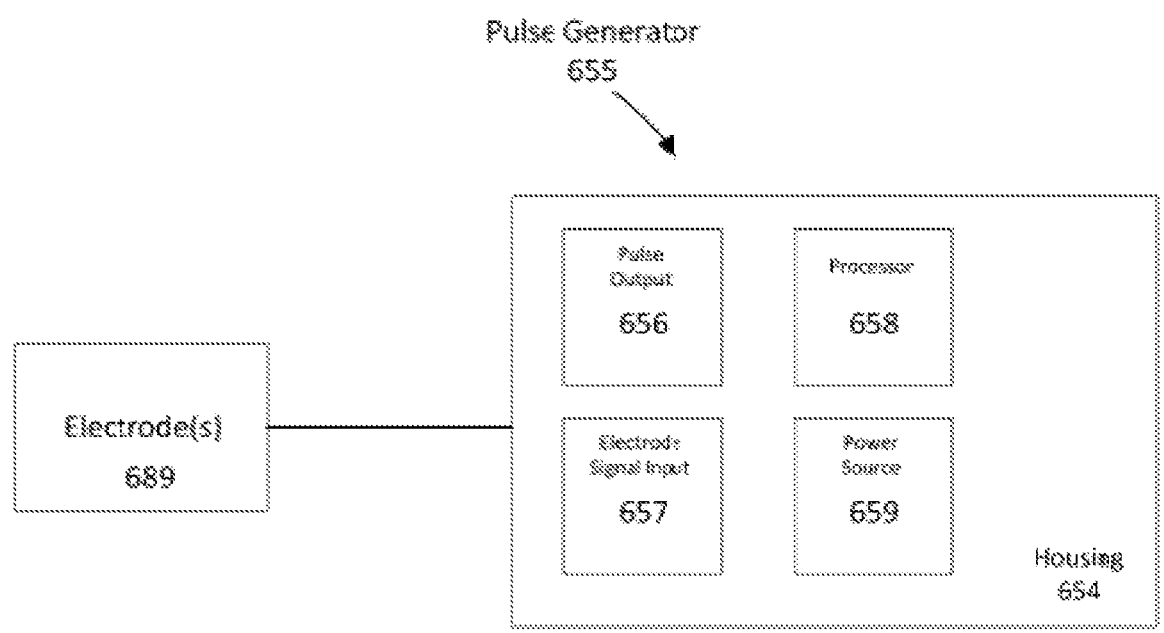
FIG. 18 is a schematic illustration of an example pulse generator.

FIG. 18 illustrates schematically an example pulse generator 655. As shown, the pulse generator 655 includes a housing containing a power source 659, a processor 658, a pulse output 656 and an electrode signal input 657. The power source 659 is configured to provide power to the one or more electrodes 689 to pace the heart. For example, in use, the power source 659 can generate electrical pulses and deliver those pulses to the one or more electrodes 689 via the pulse output 656, which is in operable communication with the one or more electrodes 689. The electrode signal input 657 is configured to receive signals from the one or more electrodes 689 for hemodynamic monitoring, as discussed in further detail herein, and those signals can be processed at the processor 658. Although not shown, in some embodiments, the pulse generator 655 can include a memory. The memory can be, for example, a memory buffer, a hard drive, a RAM, a ROM, an EPROM, and/or the like. In some embodiments, the memory stores instructions to cause the processor to execute modules, processes, and/or functions associated with controlling signals sent from and received at the pulse generator 655. For example, the memory can store instructions, information, and/or data associated with a control system.

The processor can be any suitable processing device configured to run or execute a set of instructions or code. For example, the processor can be a GPP, CPU, APU, an application specific integrated circuit (ASIC), a field programmable array, and/or the like. The processor can be configured to run or execute a set of instructions, code stored, for example, in a memory included in the pulse generator 655. For example, the processor 658 can process and/or control the pulse signals generated by and sent from the pulse generator 655, and process and/or control the signals received at the pulse generator 655 from the one or more electrodes 689.

In alternative embodiments, instead of or in addition to routing an electrode lead from the electrode through a tether lumen, the tether itself can act as an electrode lead. In such embodiments, for example, the tether can have suitable electrical conductive properties to convey electrical signals to/from the pulse generator and the implanted valve. With the tether acting as a lead, coupled to, for example, the implanted prosthetic valve, and extending outside the heart, e.g., to a thoracotomy region, a surgeon can access the lead and/or data from a pulse generator coupled to the lead for diagnostic purposes, as described above.

In alternative embodiments, instead of or in addition to disposing one or more electrodes along or about the tether as shown and described in previous embodiments, an array of electrodes can be distributed about the tether and/or the prosthetic valve, for example, within the left ventricle of the heart. In such embodiments, for example, an umbrella or spider-like array of wires having electrodes can extend or emanate radially from the tether and/or the prosthetic valve. In this manner, electrodes for pacing and/or measuring can reach locations within the heart not reached by the tether and/or the prosthetic valve alone. Further, extending electrodes along such an array of wires may provide for additional points of contact between the electrodes and various tissues or portions of the heart. An example embodiment having such an electrode array is illustrated in FIG. 19.

Figure 19:
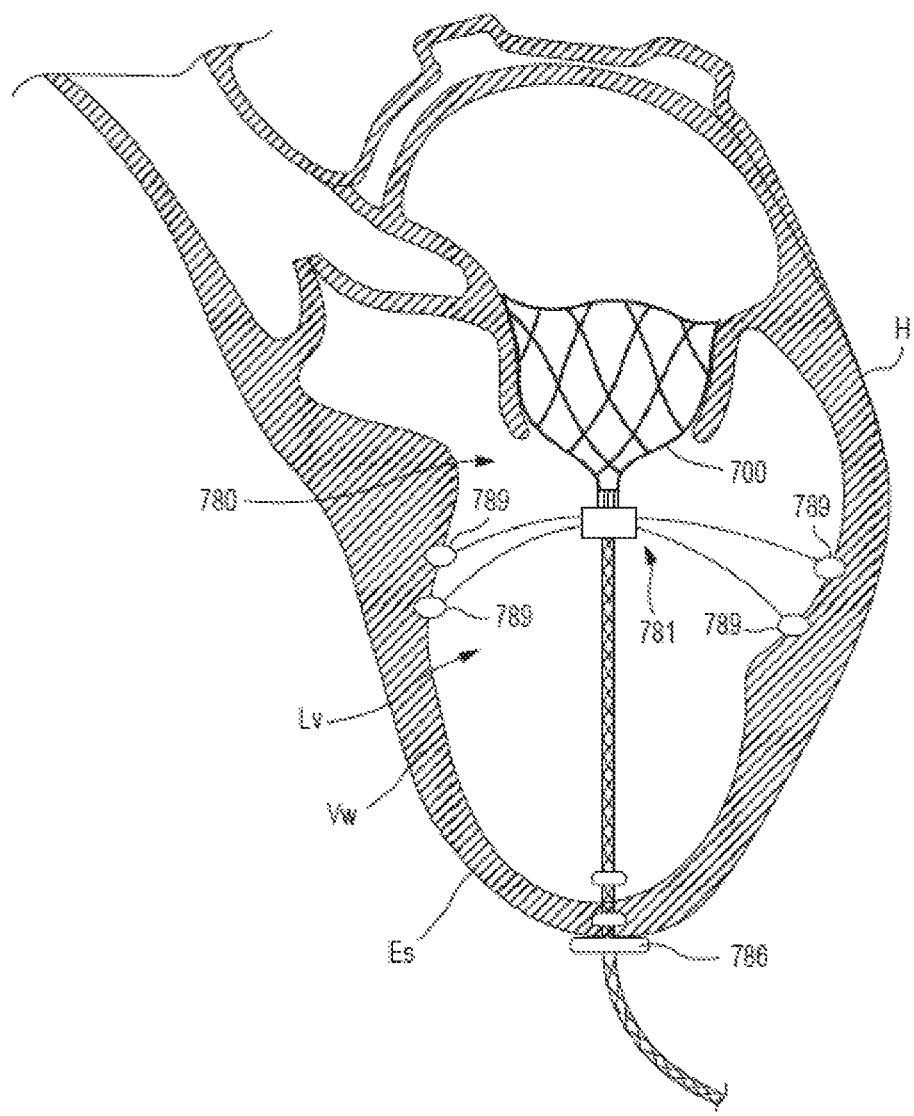
FIG. 19 illustrates in cross-sectional front view a portion of a heart having a valve-tether with an electrode array implanted therein, according to an embodiment.

The prosthetic valve 700, the valve-tether 780, and the apical pad 786 shown in FIG. 19 can be constructed the same as or similar to the other prosthetic valves, valve-tethers, and apical pads described herein, and can function in a similar manner. Thus, some details regarding the valve 700, the valve-tether 780, and the apical pad 786 are not described below. It should be understood that for features and functions not specifically discussed, those features and functions can be the same as or similar to the valves, valve-tethers, and apical pads described herein. In this embodiment, as shown, with the valve-tether 780 implanted within the heart, an electrode array 781 is coupled to the valve-tether 780 such that the electrodes 789 extending from the valve-tether 780 are in physical contact with a tissue portion of the heart H. In this manner, the electrodes 789 can convey electrical signals (e.g., to pace and/or defibrillate) to the heart tissues in contact with the electrodes 789. In alternative embodiments, any suitable number of electrodes and array extensions can be used. Further, although in this embodiment the electrode array 781 is shown as being coupled directly to the connection point between the valve and the tether, in alternative embodiments, an electrode array can be coupled to any suitable portion of the valve-tether, e.g., depending on where the operator wants the electrodes to contact heart tissue.

In alternative embodiments, a prosthetic heart valve may not include a tether coupled thereto or extending therefrom. In such embodiments, the prosthetic heart valve can include one or more electrodes configured to sense signals associated with hemodynamic monitoring, as described above. Further, as no tether is included to transmit signals from the one or more electrodes to a monitoring device (e.g., a pulse generator), in such embodiments, the prosthetic heart valve and/or the one or more electrodes can be configured to transmit the signals wirelessly to a monitoring device outside the patient's body (e.g., worn by the patient or completely physically separate and not in physical contact with the patient). In some embodiments, the prosthetic heart valve can include a wireless transmitter configured to transmit the one or more signals to the monitoring device. In any of the embodiments described herein, the signals can be transmitted upon demand (e.g., in response to a user-request) or automatically periodically, e.g., in accordance with pre-defined instructions).

In alternative embodiments, any of the devices described herein can be operably coupled to and/or used in conjunction with a coronary sinus lead implanted within a coronary sinus of the patient's heart. The coronary sinus lead can be used in a manner similar to the electrodes described here, such as, for example, for pacing the heart and/or for cardiac diagnostic purposes.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. A method, comprising:
delivering to a valve annulus of a heart a prosthetic heart valve having a body expandable from a collapsed, delivery configuration to an expanded, deployed configuration, the prosthetic heart valve having a plurality of prosthetic leaflets being positioned within the body;
after the delivering, causing the prosthetic heart valve to move from the delivery configuration to the deployed configuration;
with the prosthetic heart valve disposed in the valve annulus and in its deployed configuration, securing an anchoring tether extending from the prosthetic heart valve to a wall of the heart such that an electrode coupled to the anchoring tether is positioned at a location within a left ventricle of the heart;
sensing an electrical signal with the electrode;
conveying the electrical signal from the anchoring tether within the heart to a location outside the heart, and
monitoring a hemodynamic condition of the heart based on the electrical signal.

2. The method of claim 1, wherein:
the securing the anchoring tether includes coupling an epicardial pad device to the anchoring tether and securing the epicardial pad device to an apex region of the heart.

3. The method of claim 1, wherein the valve annulus is one of a mitral valve annulus, an aortic valve annulus, or a tricuspid valve annulus.

4. The method of claim 1, wherein:
the hemodynamic condition is selected from the group consisting of a dimension, volume, or blood pressure within the left ventricle of the heart based on the electrical signal.

5. The method of claim 1, wherein monitoring the hemodynamic condition of the heart based on the electrical signal includes sending diagnostic information via wireless communication to a receiver disposed outside the heart.

6. The method of claim 5, wherein the diagnostic information is based on the electrical signal sensed by the electrode coupled to the anchoring tether.

7. The apparatus method of claim 1, wherein the electrode is in electrical communication with a diagnostic device configured to receive electrical signals from the electrode.

8. The method of claim 1, wherein the anchoring tether is formed of an electrically conductive material, and conveying the electrical signal from the anchoring tether includes conveying the electrical signal via the electrically conductive material.

9. The method of claim 1, wherein the anchoring tether includes a lumen, and conveying the electrical signal from the anchoring tether includes conveying the electrical signal via a lead positioned within the lumen of the anchoring tether.

\* \* \* \* \*